(12) United States Patent
Paul et al.

(10) Patent No.: US 7,060,170 B2
(45) Date of Patent: Jun. 13, 2006

(54) BRIDGES, ELEMENTS AND JUNCTIONS FOR ELECTROOSMOTIC FLOW SYSTEMS

(75) Inventors: Phillip H. Paul, Livermore, CA (US); David W. Neyer, Castro Valley, CA (US)

(73) Assignee: Eksigent Technologies LLC, Livermore, CA (US)

( * ) Notice: Subject to any disclaimer, the term of this patent is extended or adjusted under 35 U.S.C. 154(b) by 317 days.

(21) Appl. No.: 10/137,215

(22) Filed: May 1, 2002

(65) Prior Publication Data
US 2003/0206806 A1 Nov. 6, 2003

(51) Int. Cl.
*G01N 27/447* (2006.01)
*F04F 11/00* (2006.01)

(52) U.S. Cl. .................. 204/450; 204/600; 204/454; 422/100; 417/48

(58) Field of Classification Search ............ 204/450, 204/454, 600, 601; 422/100; 417/48, 50; 137/806
See application file for complete search history.

(56) References Cited

U.S. PATENT DOCUMENTS

| | | | |
|---|---|---|---|
| 3,923,426 A | | 12/1975 | Theeuwes |
| 5,573,651 A | | 11/1996 | Dasgupta et al. |
| 6,012,902 A | | 1/2000 | Parce |
| 6,080,295 A | * | 6/2000 | Parce et al. ............. 204/451 |
| 6,090,251 A | * | 7/2000 | Sundberg et al. ........ 204/453 |
| 6,174,675 B1 | * | 1/2001 | Chow et al. .............. 435/6 |
| 6,287,440 B1 | * | 9/2001 | Arnold et al. ........... 204/450 |
| 6,719,535 B1 | * | 4/2004 | Rakestraw et al. ....... 417/50 |

FOREIGN PATENT DOCUMENTS

| | | |
|---|---|---|
| WO | WO 95/15489 | 6/1995 |
| WO | WO 98/00705 | 1/1998 |
| WO | WO 99/16162 | 4/1999 |
| WO | WO 00/55502 | 9/2000 |
| WO | WO 00/79131 | 12/2000 |

OTHER PUBLICATIONS

Gan et al, Mechanism of porous core electroosmotic pump flow injection system and its application to determination of chrominum (VI) in waste-water. Talanta 51 (2000) 667-675. Month unavailable.*

Wijnhoven et al, Preparation of Photonic Crystals Made of Air Spheres in Titania, Science, 281, Aug. 7, 1998, 802-804.*

(Continued)

*Primary Examiner*—Kaj K. Olsen
(74) *Attorney, Agent, or Firm*—Jeffrey G. Sheldon; Sheldon & Mak

(57) ABSTRACT

In accordance with the present invention, stable electroosmotic flow systems and methods for designing the same are disclosed. The invention provides electroosmotic flow systems comprising electroosmotic flow elements, including bridge elements, that have matching flux ratios, i.e., when two or more elements of an electroosmotic flow system are in fluidic and electrical communication at a junction, the flux ratio for each of the elements is selected so that the difference in flux ratios of any two elements is less than a target value. The invention also provides methods for designing such systems. Also disclosed is a novel design for the terminal portions of electroosmotic flow (EOF) and bridge elements and for junctions in electroosmotic flow systems, whereby the elements are designed so that the terminal current flux is much smaller than the element current flux.

75 Claims, 9 Drawing Sheets

OTHER PUBLICATIONS

Ma et al, *A review of zeolite-like porous materials*, Microporous and Mesoporous Materials 37, (2000), Month unavailable, 243-252.*

Drott et al, *Porous silicon as the carrier matrix in microstructed enzyme reactors yeilding high enzyme activities*, J. Micromech. Microeng. 7 (1997), Month unavailable, 14-23.*

Peters et al, *Molded Rigid Polymer Monoliths as Separation Media for Capillary Electrochromatography*, Anal. Chem. 1997, Month unavailable, 69, 3646-3649.*

O. Jessensky, F. Muller, U. Gosele, *Self-Organized Formation of Hexagonal Pore Structures in Anodit Alumina*, J. Electrochem. Soc., vol. 145, No. 11, Nov. 1998.

O. Kedem, A. Katchalsky, *Permeability of Composite Membranes*, Farady Soc. London Trans 59 (63).

R.J. Gross, J.F. Osterle, *Membrane Transport Characteristics of Ultrafine Capillaries*, The Journal of Chemical Physics, vol. 49, No. 1, Jul. 1, 1968.

Marshall Fixman, *Charged macromolecules in external fields. I. The Sphere*, J.Chem. Phys. 72(9), May 1, 1980.

Yonosuke Kobatake, Hiroshi Fujita, *Flows Through Charged Membranes. I. Flip-Flop Current vs Voltage Relation*, The Journal of Chemical Physics, vol. 40, No. 8, Apr. 15, 1964, pp. 2212-2218.

Yonosuke Kobatake, Hiroshi Fujita, *Flows Through Charged Membranes. II. Oscillation Phenomena*, The Journal of Chemical Physics, vol. 40, No. 8, Apr. 15, 1964, pp. 2219-2222.

David Linton Johnson, Joel Koplik, Roger Dashen, *Theory of dynamic permeability and tortuosity in fluid-saturated proous media*, J. Fluid mech. (1987), vol. 176, pp. 379-402.

John O'M. Bockris, Amulya K.N. Reddy, *Modern Electrochemistry*, vol. 2, pp. 1054-1061.

Albert P. Phillpse, *Solid opaline packings of colloidal silica spheres*, Journal of Materials Science Letters 8 (1989) 1371-1373, month unavailable.

T. Yazawa, *Present Status and Future Potential of Preparation of Porous Glass and its Application*, Key Engineering Materials vol. 115 (1996) pp. 125-146, month unavailable.

Kazuki Nakanishi, Naohiro Soga, *Phase separation in silica sol-gel system containing polyacrylic acid; I. Gel formation behavior and effect of solvent composition*, Journal of Non-Crystalline Solids 139 (1992) 1-13, month unavailable.

Sangryoul Park, *Electrochemical Detection For Capillary Electrophoresis*, Submitted to the Dept. of Chemistry and the Faculty of the Graduate School of University of Kansas inpartial fulfilment of the requirements for the degree of Doctor of Philosophy, 1996, month unavailable.

* cited by examiner

BRIDGES, ELEMENTS AND JUNCTIONS FOR ELECTROOSMOTIC FLOW SYSTEMS

RELATED APPLICATION DATA

There is no related application data.

FIELD OF THE INVENTION

This invention relates to electrokinetic systems in general and, in particular, to electroosmotic flow systems.

BACKGROUND OF THE INVENTION

In electrochemical systems, salt- or simple-bridges have been widely employed as a means to isolate electrodes and electrode byproducts from the working fluid, or more generally to isolate one electrochemical environment from another while maintaining ionic communication. A common example is the porous tip of a pH probe. In electroosmotic flow systems, a bridge is used as an ionic conductor that separates the working fluid from the fluid that is in direct contact with the electrodes. The prior art discloses several types of bridges.

For example, Theeuwes discloses the use of membrane bridges between the electrodes and working fluid in an electroosmotic pump. F. Theeuwes, Electroosmotic pump and fluid dispenser including same, U.S. Pat. No. 3,923,426 (1975). The membrane material is a sulfonated polymer having a relatively high zeta potential and very fine pores. The Theeuwes device is essentially a double-reservoir design with the outer (electrode) and inner (working fluid) reservoirs separated by the membrane. The membranes are selected for a very high charge-ratio (defined infra) and selectivity to positive ions (for example, Ag+ and H+ in the Theeuwes case, which thus inhibit current-driven growth of silver dendrites on silver: silver-chloride electrodes).

Seoul discloses a double reservoir bridge design for use in capillary electrophoresis where the outer reservoir contains a platinum wire electrode embedded in a Nafion resin. B. S. Seoul, *Electrochemical detection for capillary electrophoresis* (Doctoral dissertation, U. Kansas, 1996) pp. 136–141. The objective is to minimize the degradation of analytes by peroxides generated at the anode electrode. Nafion is a sulfonated fluorocarbon polymer that is either solid or very fine pored. It acts as an ionic conductor that is highly selective to positive ions and thus exhibits a very high charge-ratio, implying that current through this material is essentially carried solely by transport of positive ions. This is quite different from current flow in a fluid, where current is carried by transport of both positive and negative ions. Seoul's configuration prevents peroxides generated at the anode electrode from reaching the working fluid. However, the electrode/Nafion current is still carried by H+ ions and, thus, the configuration does nothing to inhibit the pH and ionic strength evolution of the fluid in the inner reservoir.

Desiderio discloses a double reservoir bridge design (similar to that used by Wallenborg infra) for use in capillary electrophoresis where the outer reservoir contains a platinum wire electrode. C. Desiderio, S. Fanali and P. Bocek, "A new electrode chamber for stable performance in capillary electrophoresis," *Electrophoresis*, 20, 525–528 (1999). The inner and outer reservoirs are separated by a plug of glass wool that serves as the bridge. The object is to minimize the evolution of inner reservoir fluid and thus maintain more constant working fluid properties. The glass wool plug is a porous material having a zeta potential. However, the pore sizes of the conduit and the plug material are sufficiently large that the charge-ratio is negligible. The plug is intended to prevent gross mixing between the outer (electrode) and inner (working fluid) reservoirs.

Ramsey discloses on-chip bridges as a means of making electrical connections in fine microchannels without introducing the gases associated with electrode electrolysis. J. M. Ramsey, S.C. Jacobson, C. T. Culbertson and R. S. Ramsey, "Microfabricated interchannel electrical contacts for material transport control," *Micro Total Analysis Systems* 2000, A. van den Berg Ed. (Kluwer Academic, Dordrecht, The Netherlands, 2000) pp. 213–216. Ramsey employs an etched glass chip that is bonded to a glass cover using a sodium silicate interlayer. This interlayer acted as a bridge between two adjacent fluid-filled channels on the chip (channel separation of 3 to 10 microns). This type of bridge falls into the selective ion conducting and flow impermeable class. During the bonding process, the sodium silicate mixture (often called water glass) dries out and forms a very fine pored sodium silicate glass (high positive charge-ratio). When wetted this material acts as a solid ionic conductor that, owing to the negative zeta potential of the glass, preferentially transports positive ions. Thus, the current in this material is primarily carried by positive ions, which is quite different from the bulk fluid where the current is carried by a mix of ions.

The electroosmotic flow channels in Ramsey are sufficiently large that the channel charge-ratio is negligibly small whereas Ramsey's bridges have a high positive value of the charge ratio. This leads to a concentration of positive ions (hence increased ionic strength) on the side of the bridge facing the cathode terminal reservoir and a depletion of negative ions (hence decreased ionic strength) on the side of the bridge facing the anode terminal reservoir.

Paul discloses a bridge to make ionic connections to high pressure junctions in electrokinetically pumped systems. P. H. Paul, D. W. Arnold, D. W. Neyer and K. B. Smith, "Electrokinetic pump applications in micro-total analysis systems, mechanical actuation to HPLC," *Micro Total Analysis Systems* 2000, A. van den Berg Ed. (Kluwer Academic, Dordrecht, The Netherlands, 2000) pp. 583–590. The bridge allows the electrode to be removed from the working fluid at a junction in a pressurized microchannel. The bridge is formed from a short section of phase-separated and acid-etch glass (e.g. Vycor or Shirasu porous glass). It has nominal 4 nm pores. For the given conditions (nominally 10 mM or less fluid ionic strength) the bridge has very low permeability to pressure- and electroosmotically-driven flow but is subject to a high degree of charge-layer overlap and, thus, ion-selective current transport. The fine-pored glass bridge is highly charge selective and preferentially transports positive ions, owing to the nanometer-scale pores and the high negative zeta potential of the bridge material. Thus, the current in this material is primarily carried by positive ions whereas the current carried in the pump element, based on a predictive model, is carried near-equally by positive and negative ions (Paul shows a silica pump element supplied with nominal pH 7.5 sodium-phosphate buffered fluid). The imbalance in charge fluxes creates a condition where the fluid flowing out of the pump/bridge junction is at a depleted sodium concentration resulting in a lower degree of phosphate ionization. Thus, the working fluid is at a lower ionic strength and a much lower pH than the source reservoir fluid.

Wallenborg describes various types of bridges for mitigating evolution of reservoir fluid in chip-based empty-channel micellar electro-chromatography (see infra for definition of "empty"). S. R. Wallenborg, C. G. Bailey and P. H. Paul, "On-chip separation of explosive compounds—divided reservoirs to improve reproducibility and minimize buffer depletion," *Micro Total Analysis Systems* 2000, A. Van den Berg Ed. (Kluwer Academic, Dordrect, The Netherlands, 2000) pp. 355–358. Wallenborg discloses that in a device comprising a microchannel connected between two terminal reservoirs, oscillations in both current and flowrate are observed. By replacing each terminal reservoir with two reservoirs in series connected with a bridge, the oscillations are significantly reduced with nano-porous bridge materials (specifically: 4 nm pore Shirasu porous glass, 4 nm pore Vycor porous glass, or a nano-porous polymer monolith). However, the use of the bridge introduces a systematic time-variation in ionic strength and hence variations in conductivity and electroosmotic mobility. A larger pore glass material (specifically 70 nm pore Shirasu porous glass) reduces the variation in ionic strength. The small-pored media introduces ion-selective current transport through the bridge and hence the variation in fluid conductivity. This effect is reduced but not eliminated using the larger-pored media that also allows electroosmotic flow. In very fine pored bridge materials the fractional selectivity to current-driven charge transport by ions of one sign is about unity, whereas in the bulk working fluid, this same selectivity is generally about 10% or less owing to minor differences in ion mobilities.

Gan describes the use of a thin cellulose-acetate membrane as a bridge-like structure to isolate fluid in direct contact with the electrodes from fluid flowing in an electroosmotic pump driven by current supplied from the same electrodes. W. Gan, L. Yang, Y. He, R. Zeng, M. L. Cervera and M. de la Guardia, "Mechanism of porous core electroosmotic pump flow injection system and its application to determination of chromium (VI) in waste water," *Talanta* 51 pp. 667–675 (2000) which references Y. Z. He and W. E. Gan, Chinese Patent ZL 97212126.9 (1998). A membrane of this type and structure acts to reduce gross mechanical mixing of the fluids. This type of bridge provides the same effect as the glass wool plug used by Desiderio.

Parce describes the use of bridges (termed by Parce a 'flow restrictor' or 'flow restrictive element') incorporated into microchannel systems applied to placement of electrodes within the fine channels of the system to avoid electrolysis therein. J. W. Parce, Micropump, U.S. Pat. No. 6,012,902 (2000), col. 8, 11. 5–10. See also J. W. Parce, Micropump, WO99/16162 (1999). Parce describes the flow restrictive element as '. . . provided to allow passage of current between the electrodes, while substantially preventing flow . . .' Id. at col. 8, 11.36–39. Parce further recites that '[i]n at least a first aspect, the flow restrictive element includes a fluid barrier that prevents flow of fluid, but permits transmission of electrons or ions, e.g. a salt bridge.' Id. at col. 8, 11. 44–47. Parce discloses the following types of bridges: agarose or polyacrylamide gel plugs, Id., col. 8, 1. 47; a series of parallel channels each having a much smaller cross sectional area than the remaining channel structure, to reduce the electroosmotic flow through the side channel (bridge) (for example, the much smaller cross sectional area channels have at least one cross sectional dimension in the range from 0.001 to 0.05 microns when the other channels in the system have a size range of about 20 to 100 microns) Id., col. 8, 11. 49–65; and a side channel (bridge) which optionally includes a plurality of side parallel channels, and also substantially lacks surface charge to reduce or eliminate any electroosmotic flow. Id., col. 8, 1. 66 to col. 9, 1. 2.

Parce also describes a configuration that uses two pumping channels (having substantially different charge magnitude and/or sign from each other) that are connected in electrical series. Id., col. 9, 1.3 to col. 10, 1.12. In this configuration, the difference in zeta potential produces a difference in flowrates that results in production of a pressure at the common junction that is used to induce a pressure-driven flow through a third channel connected to this common junction. The phenomena of pressure generation due to variation of zeta potential along a channel is a well-known process [see for example, J. L. Anderson and W. K. Idol, "Electroosmosis through pores with nonuniformly charged walls," *Chem. Eng. Commun.*, 38 pp. 93–106(1985)].

Because the pumping channels recited by Parce are very large, the channel charge-ratio is negligibly small. Further the finer side channels (bridge) are described as substantially lacking surface charge, this implies a negligibly small value for the charge ratio. The system described by Parce thus operates in the limit of negligible charge-layer effects hence negligible charge-layer-driven net solute transport.

Dasgupta describes the use of a 'membrane grounding joint' made of Nafion ion exchange tubing at the end of an empty silica capillary. P. K. Dasgupta and S. Liu, Apparatus and method for flow injection analysis, U.S. Pat. No. 5,573, 651 (1996). The grounding joint acts as a bridge to make an electrical connection to the empty capillary that in turn serves as an electroosmotic-flow-pump (EOF pump). Such a bridge is highly selective to positive ion migration (i.e. substantial positive charge ratio) and therefore not matched with the empty capillary electroosmotic element (i.e. negligibly small charge-ratio). As direct evidence of the effect of this mismatch, Dasgupta observes that if the outlet hydrostatic resistance to an EOF pump is increased, the resulting drop in flow rate is accompanied by a decrease in current at the same applied voltage (in fact, this phenomenon is not observed for any uniform ionic strength fluid). The ionic flux mismatch incurred through the use of a Nafion bridge, produces a decrease in ionic strength at the bridge joint. Under normal operation this fluid is carried downstream. With an increase in outlet hydrostatic resistance and hence an increase in backpressure, some fluid from this joint is backflushed into the pumping element. The introduction of the lower concentration, hence lower conductivity, fluid yields the observed reduced current. Without an ionic mismatch at the bridge, the current would be expected to stay substantially constant as the hydrostatic resistance is varied.

To summarize, prior art bridges in electroosmotic flow systems generally fall into four classes: (1) porous media or a membrane with large pores that allows pressure- and electroosmotically-driven flow but inhibits gross mechanical mixing; (2) non-specific ion conducting and flow impermeable media (e.g. a classic salt bridge); (3) porous media with relatively fine pores that greatly restrict pressure- or electroosmotically-driven flow (e.g. pores of order 5 nm diameter or less); and (4) specific ion conducting and flow impermeable media. In the first and second classes and in the third class for materials without a zeta potential, the charge-ratio is negligibly small and, therefore, the material adds little selective current-driven transport of particular ions. In the third class for media with a zeta potential and in the fourth class, the charge-ratio is substantial and the bridge materials are strongly ion-selective and, therefore, the electrode has been removed from direct contact with the working fluid but the action of the bridge may concentrate select ions, thus evolving the working fluid and possibly creating a condition leading to unsteady state operation.

Most of the prior art in electroosmotically-driven flow systems is in the area of interconnected empty microchannel elements, where the conduit diameter is large enough that flux imbalances are essentially negligible (i.e. negligibly small values of the charge-ratio). Thus, the prior art does not teach stable electroosmotic flow systems or bridges for such systems for the substantial charge ratio regime. In fact, the prior art is predominantly concerned with bridge designs for systems where the charge-ratios are negligible for all elements in the system. Bridge designs for substantial charge-ratio cases (the third and fourth classes supra) actually compound the problem of differential ion flux and hence concentration evolution. Therefore, there is a need for designing stable electroosmotic flow systems that contain elements that are subject to some degree of charge-layer overlap leading to unequal flux ratios.

SUMMARY OF THE INVENTION

The present invention satisfies the aforementioned needs by providing stable electroosmotic flow systems and methods for designing the same. In a first aspect of the invention, the electroosmotic flow systems of the invention comprise electroosmotic flow elements, including bridge elements, that have matching flux ratios (defined infra). Thus, when two or more elements of an electroosmotic flow system are in fluidic and electrical communication at a junction, the flux ratio for each of the elements is selected so that the difference in flux ratios of any two elements is less than a target value. The target value is often selected to be near zero. The invention also provides for methods for designing such systems.

In a second aspect of the invention, a novel design is provided for the terminal portions of electroosmotic flow (EOF) and bridge elements and for junctions in electroosmotic flow systems. In accordance with this aspect of the invention, the elements are designed so that the terminal current flux is much smaller than the element current flux. This is accomplished by selecting element geometries wherein the surface area of the terminal portion of an element is much greater than the effective cross-section area of the element, e.g., from 50% to 200% greater.

The invention also provides for a novel layout of electroosmotic flow system junctions to increase flow past the surface of the terminal portion(s) in the junction.

DETAILED DESCRIPTION OF THE PREFERRED EMBODIMENTS

Figure 1:
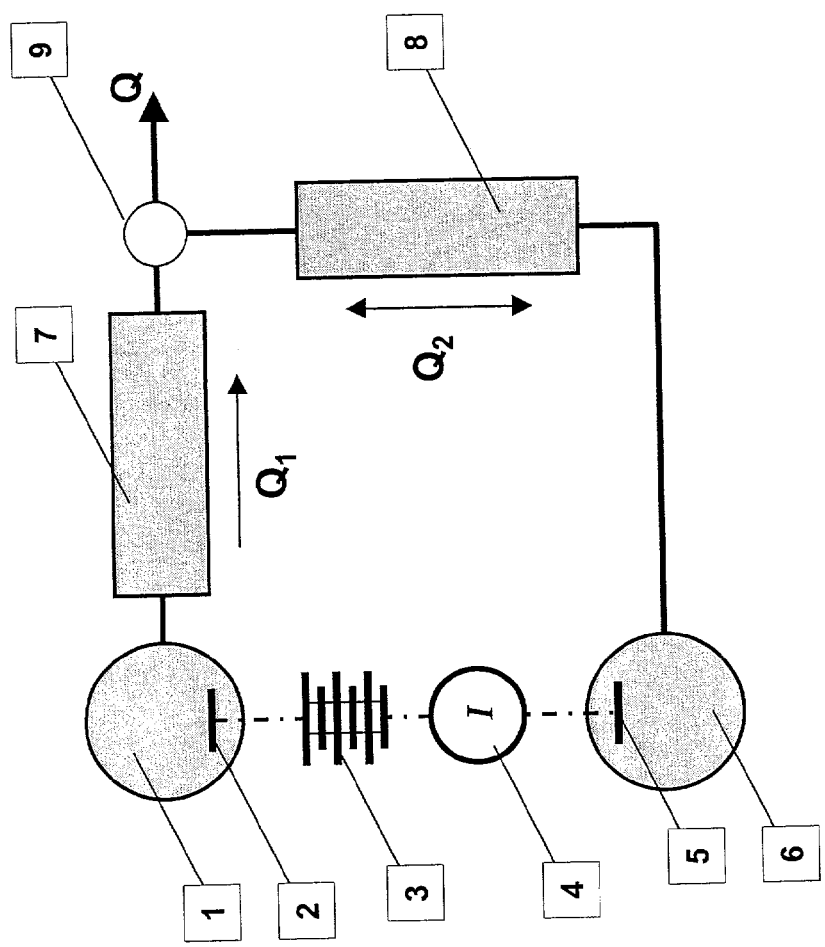
FIG. 1 is a schematic of a two element electroosmotic flow system.

1. EOF Systems with Matching Flux Ratios

The invention is generally applicable to cases where a current is passed through a conducting liquid (as opposed to the devices of the invention, a pH probe or a galvanometric/amperometric reference electrode makes electrical contact but does not carry a current). Such cases include, but are not limited to: electrokinetic pumps, electrokinetic flow controllers, capillary or on-chip microchannel electrophoresis, capillary or on-chip microchannel electro-chromatography, electro-dialysis and electroosmotic flow systems.

The interaction between an electrolyte and a solid dielectric or insulator produces several effects including charging of the interface and the formation of a so-called double layer. Consider the case where the surface displays some net charge. This may be the result of the solid acting as a Lewis or Bronsted acid or base that becomes charged as a result of natural electrochemical reactions with the electrolyte or may be the result of charged species being adsorbed onto the surface. In either case, the charge at the interface is counterbalanced by an equal and opposite charge composed of ions in the solution. Finite size of ions and thermal motion prevents this counter charge from lying immediately adjacent to the surface, and the result is a 'diffuse charge layer' that has a thickness of about a Debye length. The presence of this charge layer leads to several effects including electrokinetic phenomena.

Amongst the various types of electrokinetic phenomena is electroosmotic flow (EOF, sometimes termed electroosmosis), which is produced when a tangential electric field is applied to a surface bearing a diffuse charge layer. The tangential electric field acting on the diffuse charge layer produces a net force hence a relative motion between the surface and the liquid bearing the diffuse charge layer. This motion can be transferred by viscous action to adjacent net neutral liquid. Electrokinetic systems are characterized by a zeta potential, which is the potential difference across the mobile part of the diffuse charge layer. The value of the zeta potential depends on the composition of the electrolytic solution (specifically on the permittivity, ionic content and pH of the solution, and the identify of ions within the solution) and on the charge density on the surface.

Electroosmotic flow (including electrophoresis, streaming potential, streaming current, sedimentation potential), may be generated using a wide variety of fluids and dielectric surfaces. Details related to fluid and dielectric material properties, geometry and other physical characteristics of electroosmotic flow systems in general can be found in co-pending U.S. Patent Publication No. 2002/0189947, the entire contents of which are incorporated by reference herein.

An electroosmotic flow system comprises one or several electroosmotic flow elements (defined infra) connected in series and carrying a common current. Power is supplied via electrodes located at the terminal ends of the system, possibly in terminal reservoirs. Flow through the system may be induced by electroosmotic effects (i.e. electroosmotic or electrokinetically-induced pressure-driven flow), possibly in combination with externally imposed pressure-driven flow.

A conduit has an inlet and an outlet through which current and/or fluids may pass. All conduit geometries are contemplated to be within the scope of the invention. For example, the cross-section of the conduit may be cylindrical, rectangular, square, hexagonal or any other shape or any combination of shapes. In general, a conduit has an inlet and an outlet through which current or fluids pass but its remaining sides are impermeable to the flow of current or liquid. Channels and micro-channels are examples of such conduits. However, the invention also contemplates within its scope, conduits characterized by a free liquid surface. Trench-like channels that have an inlet and an outlet and at least one other side that is open to liquid flow are also contemplated to be within the scope of the invention.

The length L of the conduit is defined as the distance between the inlet and the outlet measured along the mean flow/current streamline. The effective cross-sectional area A of the conduit is defined as: $A=LF/\rho\sigma$ where F is the formation factor (defined infra) of any porous media within the conduit, $\sigma$ is the electrical conductivity of the liquid filling the conduit and $\rho$ is the electrical resistance of the liquid saturated conduit. The surface area of a face of an empty conduit is taken to be the total geometric surface area through which current and/or flow passes into or out of the conduit. A face of a conduit containing porous media is determined by the interface between the porous media of the conduit and the liquid or other porous media beyond that of the conduit. The porous media of a conduit may extend beyond the flow-impermeable boundaries of a conduit. The face of this porous media need not be planar. The total surface area of a face of a conduit containing porous media is the total geometric area of the face that passes current and/or flow. To this end any microscopic irregularities, being features having length scales less than about 100 Debye lengths or less than about one dynamic pore scale, are treated as smooth.

The conduit may or may not contain a porous medium. Throughout this specification, a conduit that does not contain any porous medium is referred to as an "empty" conduit. However, an empty conduit may contain liquid. In fact, in the general case, because the invention relates to electroosmotic flow systems, empty conduits are completely filled with a liquid, such as the working liquid. The word "empty" signifies the absence of any porous material in the conduit.

An electroosmotic flow element comprises a conduit that may be a single conduit or an array of parallel conduits, that may or may not contain a porous medium. The conduit contains a fluid, e.g., the working fluid defined below. In all the embodiments described below, the fluid is a liquid. The EOF element is characterized by a zeta potential (that may be negligibly small) and carries a current. The EOF element is also characterized by a dynamic pore scale (the hydraulic diameter for a cylindrical conduit) and by a wetted-surface-to-wetted-volume ratio. The terms "electroosmotic flow element," "EOF element" and "element" are used interchangeably throughout the specification and should be construed to mean "electroosmotic flow element."

A bridge or bridge element is that part of an electroosmotic flow system that connects an electrode reservoir to the remainder of the electroosmotic flow system.

A flow element, as distinguished from an electroosmotic flow element or EOF element, refers to a conduit or a set of conduits through which a fluid is flowing.

The working fluid comprises a fluid that is an aqueous or an organic fluid or a mixture thereof that contains some concentrations of dissociated and ionized components. The bulk fluid is characterized by a dielectric permittivity and by the concentrations of the ionized species, hence by an ionic strength and by a Debye length. Given the mobilities of the ionized species, the fluid is also characterized by the relative difference in bulk fluid ion mobilities (here this relative difference, denoted by the symbol $R_f$ is defined as the positive less the negative ion bulk fluid mobilities divided by their sum).

In preferred embodiments, the electroosmotic flow elements of the invention comprise conduits that contain or are packed with porous media. Examples of porous materials for use in the invention include but are not limited to the following porous materials:

Packed particles where the particles may be glass or ceramic or polymers. The particles may be held in place (i.e. confined within a conduit) by any method known in the art, including but not limited to end-frits or other mechanical restrictions, or by cold welding under pressure, or chemical bonding, or locked-in via a sol-gel.

Synthetic porous opaline-like materials, such as those described in, for example, A. P. Philipse, 'Solid opaline packings of colloidal silica spheres,' J. Mat. Sci. Lett. 8 pp. 1371–1373 (1989), and porous materials created by using opalines as a template, as described in, for example, J. E. G. J. Wijnhoven and W. L. Vos, 'Preparation of photonic crystals made of air spheres in titania,' Science 281 pp. 802–804 (1998).

Porous materials prepared by phase separation and chemical leaching of a glass, for example the Vycor process as applied to a borosilicate or other composite glass as described in, for example, T. Yazawa, 'Present status and future potential of preparation of porous glass and its application,' Key Engineering Materials,' 115 pp. 125–146 (1996).

Porous materials prepared by solgel or aerogel process in silica, alumina, titania, zirconia and other inorganic-oxides or mixtures thereof.

Zeolite and zeolite-like porous media as described in, for example, Y. Ma, W. Tong, H. Zhou, S. L. Suib, 'A review of zeolite-like porous materials,' Microporous and Mesoporous Materials 37 pp. 243–252 (2000).

Porous materials prepared by phase separation of polymer—inorganic oxide solutions as carried out using, for example the SilicaRod process described in, for example, K. Nakanishi and N. Soga, 'Phase separation in silica sol-gel system containing polyacrylic acid I. Gel formation behavior and effect of solvent composition,' J. Non-crystalline Solids 139 pp. 1–13 (1992).

Porous materials prepared by direct machining, by lithography and etching, molding, casting, laser ablation and other methods known in the arts. Direct machining may be used to generate, e.g., regular or irregular arrays of microchannels or pillars fabricated from a material that, in combination with a desired pumping or transport liquid, gives rise to a zeta potential. Such microchannels or pillars may be used as the porous dielectric materials of the present invention.

Porous polymers prepared by film stretching, sintering, track etching, casting followed by leaching or evaporation, slip casting, phase inversion, thermal phase inversion. Like methods are often employed in the manufacture of polymer filter membranes.

Porous polymer monoliths as described in, for example, E. C. Peters, M. Petro, F. Svec and J. M. Frechet, 'Molded rigid polymer monoliths as separation media for capillary electrochromatography,' Anal. Chem. 69 pp. 3646–3649 (1997).

Porous materials prepared by anodic etching as applied to silicon, as described in, for example, J. Drott, K. Lindstrom, L. Rosengren and T. Laurell, 'Porous silicon as the carrier matrix in micro structured enzyme reactors yielding high enzyme activities,' J. Micromech. Microeng. 7 pp 14–23 (1997) or as applied to aluminum as described in, for example, O. Jessensky, F. Muller and U. Gosele, 'Self-organized formation of hexagonal pore structure in anodic alumina,' J. Electrochem. Soc. 145 pp. 3735–3740 (1998).

The porous materials may be fabricated in-conduit (or in-channel) or may be fabricated, machined or cut, and then inserted or sealed into the conduit (or channel), or, as is the case with microchannel arrays, the porous dielectric material may be machined so as to require no exogenous channel, the channel being formed by the walls of the substrate from which the array is machined. The surface properties may be altered before or after placement within a conduit (or channel).

The sign and magnitude of the zeta potential can be altered or enhanced by modification of the surface or bulk chemistry of the porous material as described in co-pending U.S. Patent Publication No. 2002/0189947 (see supra). Modification of surface chemistry is generally done by reaction with sites (e.g. silanol, hydroxyl, amine) that are present on the native material. Modification of the bulk chemistry is generally done by synthesis of a material that directly incorporates ionizable sites. Examples include but are not limited to the following:

Modification of the bulk chemistry of a polysulfone or polyethersulfone or poyletherketones to convert some portion of the S=O groups to sulfonic acids. The sulfonic acid groups then providing a strongly acidic surface site.

Modification of the bulk chemistry of PTFE to attach side chains terminated in sulfonic acid groups (Dupont product Nafion™). The sulfonic acid groups then provide a strongly acidic surface site.

Modification of the bulk chemistry of a polyethersulfone or a polyvinylidene fluoride to introduce quaternary amines. The quaternary amine groups then provide a strongly basic surface site.

Modification of the bulk or surface chemistry of a polyamide (Nylon) to provide a material with only carboxy (acidic) or amine (basic) surface sites.

Modification of a zwitterionic material (e.g. Nylon) to terminate one of the existing ionizable sites with a nonionizable end group. The material is then converted to one having only a basic or an acidic site, rather than one having both types.

Activation of a polymer material by introduction of defects or creation of cross-links via exposure to a plasma, ultraviolet or ionizing radiation. This creates reactive surface sites such as carboxyls.

Modification of surface silanol groups with methoxy- or chloro-silanes to create amino groups or sulfonic acid groups.

The conduit materials of the electroosmotic flow elements of the present invention are selected to meet requirements for mechanical strength, dielectric breakdown strength, transport or pumping liquid and liquid additive compatibility, and the capacity to retain the porous dielectric material. The possible geometries of the conduit cover the entire range from long in length and small cross section to short in length and large cross section. An example of the former geometry is a channel that may be a capillary tube or a covered microchannel formed in a substrate having cross sectional shapes including round to rectangular to rectangular with sloped or curved sides. The channel may be formed by any of the means known in the art. An example of the latter geometry is a large diameter and thin porous membrane.

The choice of pore size, topology numbers and physical geometry (e.g. conduit length and cross-sectional area) are particular to a given application, which also determines the ionic strength and buffering capacity. In general, the following considerations may be taken into account for practicing preferred embodiments of the present invention.

Use of singly valent counterions (ions with a sign opposite that of the zeta potential) for a well defined hence well-behaved zeta potential.

Use of pumping or transport or working liquid absent compounds that degrade or eliminate the zeta potential.

Use of the lowest concentration of ionic species compatible with 'minimal' double layer overlap (i.e. a concentration yielding a liquid Debye length that is less than about one-fifth the dynamic pore scale).

Use of the lowest concentration of buffering ionic species consistent with establishing and maintaining the pH of the pumping or transport liquid.

Use of ionic species that are compatible with, well soluble, and well dissociated in the pumping or transport or working liquid.

A pore size distribution that is preferably monodisperse and if polydisperse does not contain occasional large pores or defects (e.g. cracks or voids) and contains no or a minimal number of substantially smaller pores.

Use of a porous dielectric material that is less conducting than the pumping or transport or transport liquid including any additives.

Use of a porous dielectric material with a dielectric strength sufficient to withstand the potentials applied without dielectric breakdown.

Use of a porous dielectric material that is mechanically strong enough to withstand the pressures applied or generated both as regards the ability to withstand compression and collapse, and the ability to remain attached to the material of the bounding channel or conduit.

Use of a porous dielectric material that is chemically resistant and insoluble in the pumping or transport or working liquid including any additives.

Use of a channel or conduit material that is an insulator, and in particular the material should be less conducting than the pumping or transport or working liquid including any additives.

Use of a channel or conduit material with a dielectric strength sufficient to withstand the potentials applied without dielectric breakdown.

Use of a channel or conduit material that is mechanically strong enough and thick enough to withstand the pressures applied or generated.

Use of a channel or conduit material that is chemically resistant and insoluble in the pumping or transport or working liquid including any additives.

Use of a pumping or transport or working liquid with a high value of the dielectric permittivity and a low value of the dynamic viscosity.

Use of a combination of pumping or transport or working liquid, surface chemistry and additive ionic species chemistry that provides a high value of the zeta potential.

Use of a pumping or transport or working liquid that is a pure liquid or a highly miscible mixture of pure liquids.

The invention provides novel designs for and methods for designing stable electroosmotic (and electrophoretic) flow systems, which operate with minimal losses. When an electroosmotic flow system is operated under conditions where a concentration difference exists along some portion of the device, the flow and current through the device will in general be unsteady and may oscillate. Such a concentration difference may be intentionally imposed or may be created naturally, during the normal course of operation, by current-driven charge transfer. The invention is based on the pioneering discovery that instability and unsteady behavior with respect to flow, concentration and current in electroosmotic flow systems is caused by a mismatch in the flux ratios (defined infra) of the EOF elements of the flow system. Using this discovery, the invention provides, inter alia, electroosmotic flow systems that do not exhibit such unsteady state behavior. Such flow systems are characterized by elements that have matching flux ratios. Throughout the specification, the term 'matched elements' refers to elements where the values of the flux ratios of the elements is such that the difference between the flux ratio values is less than or equal to a target value. As a subset, matched elements include elements that have flux ratios that are equal to each other, i.e., the target value is zero. The term 'matching' is also to be similarly understood. Thus, matching elements are elements with flux ratios that are equal to each other or within a target value of each other.

The flux-ratio is defined as the ionized species solute displacement flux per unit current flux through an element. For conditions of negligible charge-ratio, the flux-ratio takes the value $R_f$ of the bulk fluid. The flux-ratio as defined, is independent of the current or element geometry, but is a complex function of pore size, zeta potential and ionic composition of the fluid.

Using models available in the literature, mathematical expressions can be derived for the flux ratio for a given geometry and material properties. For example, the literature provides models for evaluation of charge-layer contributions to flux ratio and ion mobilities for right-regular conduits and porous media. See, for example, 0. Kedem and A. Kalchalsky, "Permeability of composite membranes," *Faraday Soc. London*, 59 pp. 1918–1930 (1963); R. J. Gross and J. F Osterle, "Membrane transport characteristics of ultrafine capillaries," *J. Chem. Phys.*, 49 pp. 228–234 (1968); and M. Fixman, "Charged molecules in external fields," *J. Chem. Phys.*, 72 pp. 5177–5186 (1980). The mathematical relations provided in the specification are formally correct for incompressible (i.e. Mach-number less than about 0.3, hence flow velocity of less than about 0.3 times the speed of sound in the liquid) and creeping flow (i.e. flow Reynolds number less than about 5). However, the given relations are approximately accurate for the time-average flowrates for laminar flow (i.e. Reynolds numbers less than about 2000).

Further, experimental methods for observing the effects and measuring relative values of the flux ratio can also be developed. For example, consider an electroosmotic flow system that comprises a liquid-filled conduit in a dielectric material where the walls exhibit a net charge. Such a system is characterized by a net charge distribution and, hence, a potential distribution (here termed the 'static' potential and denoted by the function $\psi$) that varies spatially within the pore fluid. The effective value of the static potential at the wall is the zeta potential (denoted by $\zeta$), which, as noted above, depends on the nature of the electrolytic fluid and the solid-liquid interface. When a second electric field (here termed the 'applied' field yielding the 'applied' potential distribution) is applied along the length of the pore, the applied field produces an ionic flux (an electric current) and an electroosmotic flow.

The velocity field for the electroosmotic flow may be written as $$U = -\alpha(y_o - y)E \qquad (1)$$

where E is the local value of the applied electric field vector and $$\alpha = \epsilon kT/e\mu$$

$$y = e\psi/kT$$

where $\epsilon$, k, T, e and $\mu$ are the electric permittivity of the fluid, Boltzmann's constant, the temperature, the electron charge, and the dynamic viscosity of the fluid, respectively. The quantity $y_o$ is the value of y at the wall (i.e. the value of y with $\psi=\zeta$). The velocity field may also contain a pressure-driven component. However, the present objective is to write expressions for charge-transfer and charge-separation. Under conditions of an applied current, these processes are dominated by E-field-driven effects with little or no contribution from pressure-driven flow. Thus, the pressure-driven flow component can be neglected for purposes of the present analysis.

The flux of the i'th ionic species may be written as $$j_i = (z_i n_i - \alpha(y_o - y))C_i E \qquad (2)$$

where $z_i$, $n_i$, and $C_i$ are the signed valency, the mobility and the local concentration of the i'th species, respectively. It will be appreciated that several of the quantities in the species flux equation vary as a function of position within the pore. A representative volume element is defined as a volume element that is sufficiently small that axial (i.e. E-field directed) gradients in quantities may be well-approximated by first-order expansion terms, but sufficiently large to contain a statistically significant sample of the whole pore size distribution. Taking a formal volume average (denoted by the operator $<\ldots>$) over the representative volume elements allows the total axial current and concentration displacement fluxes to be written $$J = e\sum z_i \langle j_i \rangle \qquad (3)$$

$$J_D = e\sum \langle j_i \rangle - e\langle U \rangle \sum C_i^o \qquad (4)$$

respectively, where the summations are over all ionic species and the $C_i^o$ are the concentrations of the species in bulk fluid. The 'flux ratio' is then defined by $$R = J_D/J \qquad (5)$$

For a binary, univalent electrolyte this may be expanded to read $$R \cong \frac{R_f + \frac{4\lambda}{\Lambda}[R_f(c-1) - s - \varphi y_o(2c - 1 - 2sc/y_o)]}{1 + \frac{4\lambda}{\Lambda}[(c-1) - R_f s - \varphi y_o(2s^2/y_o - 2s)]} \qquad (6)$$

where s and c are the hyperbolic sin h and cos h functions of argument $y_o/2$. Here $\lambda$ is the Debye length in the fluid and $\Lambda$ is the dynamic pore scale and $$R_f = (n_+ - n_-)/(n_+ + n_-) \qquad (7)$$

$$\varphi = \alpha/(n_+ + n_-) \qquad (8)$$

where $n_+$ and $n_-$ are the mobilities of the positively and negatively charged ions.

For $\lambda \ll \Lambda$ or for values of the zeta potential, hence $y_o$, tending to zero, the value of R goes to the value of $R_f$. However, for a finite value of $y_o$ and the value of $\Lambda$ approaching the value of $\lambda$, R tends to limiting values of $\pm 1$ taking the sign opposite that of the zeta potential.

Extension of the these analyses to non-symmetric or polyvalent or complex electrolytes is a straight-forward exercise for anyone familiar with the science of electrochemistry.

An example electroosmotic flow system is shown schematically in FIG. 1. As can be seen, the system shown in FIG. 1 comprises a first electrode reservoir 1 that contains a working fluid that is in electrical contact with a first electrode 2, and a second electrode reservoir 6 that contains the working fluid that is in electrical contact with a second electrode 5. The system further comprises a source of current 3 electrically connected to electrodes 2 and 5 so that current can flow between the electrodes. An ammeter 4 is provided to measure the current. Electrode reservoir 1 is electrically and fluidically connected (or "connected" for short) to the first end of a first electroosmotic flow element 7. The second end of the first electroosmotic flow element 7 is connected to the inlet of junction 9, which also has a first outlet and a second outlet. The first outlet of junction 9 is connected to the first end of a second electroosmotic flow element 8. The second outlet of junction 9 may be connected to a reservoir or to a liquid collection device, which can be used to measure the flow rate of the liquid leaving the second outlet. The second end of the second EOF element, which may be a bridge, is connected to the second electrode reservoir. Denoting the first and second electroosmotic flow elements by the subscripts '1' and '2', respectively, the flow rate of the working fluid through the first EOF element is $Q_1$, that through the second EOF element is $Q_2$ and that through the second outlet is Q.

The electrode reservoirs are sufficiently large that the ionic composition of the fluid within the reservoirs may be assumed to be reasonably constant over the course of a test experiment. The reservoirs contain a simple salt, at some concentration C, dissolved in a liquid. The current source 3 may be a source of direct current. The ionic current carried through the fluid in the first and second elements will yield a displacement flux and may yield an electroosmotic flow. The direction of the applied potential and the order of the elements is such that the flow through the first element is towards the second element, and the flow through the second element is less than that through the first element. Thus there will be a net flow, Q out of junction 9 as shown in FIG. 1. The ionic concentration, C', in the liquid flowing out of the junction for three cases is:

1. For the case where the flow through the second element is negligible (i.e. $Q_1 \gg Q_2$) or for the case where the flow through the second element is away from the first element $$C' = C + (R_2 - R_1)I/eQ_1 \qquad (9)$$

where $Q_1$ is the flowrate through the first element.

2. For the case where the flow through the second element is towards the first element $$C' = C + (R_2 - R_1)I/eQ \qquad (10)$$

where Q is the flowrate out of the common junction (i.e. $Q_1 + Q_2$).

3. For the case where the flow through the first element is conserved through the second element (i.e. $Q_1 = Q_2$ and the flow through the second element is away from the first element) and hence there is no flow out of the common junction, equation 9 applies and C' is the concentration in the fluid at the junction between the elements.

The difference in the flux ratios (i.e. $R_2 - R_1$) can be determined from measurements of the total current, I, the appropriate flowrate, and given measures of C and C' (that might be derived by measuring the conductivity of the liquids). Obviously if the value of C' is about the value of C then the flux ratios are near-matched. The absolute flux ratio of one element may also be determined if the value of the flux ratio of the other element is known a priori.

As noted, the flux ratio reduces to $R_f$ for an element having a vanishingly small zeta potential or for an element having a dynamic pore scale much larger than the Debye length. For a given ionic composition of a fluid the value of $R_f$ is known. Thus, the flux-ratio of the first element can be determined by using a second element where the pore size and/or zeta potential are selected so that the flux ratio of the second element is $R_f$. For example: the second element may be a capillary or a conduit filled with a porous material where the capillary and/or porous materials are selected for relatively large dynamic pore scale (e.g. more than one micron) and vanishingly small zeta potential (e.g. Teflon, PEEK or polypropylene). The flowrate through the second element follows Darcy's law and, thus, may be calculated from a measurement of the pressure drop across the second element. The fluid in the junction subsequently flows through and saturates the second element. The ratio of current to the voltage drop across the second element is directly proportional to the conductivity of the fluid. The conductivity of the fluid at starting conditions (where the system is saturated end-to-end with reservoir fluid) provides a measure of C whereas the conductivity observed with current applied to the system provides a measure of C'. If the fluid contains a buffering solution, to determine fluid composition, in addition to conductivity, the pH of the fluid may also need to be measured.

As an illustration, consider the case of a binary univalent electrolyte. If the flowrate through the second element is negligible, the relative change in concentration may be approximated by $$\frac{C'}{C} - 1 \approx (R_2 - R_1)\frac{n_+ + n_-}{v_1} \qquad (11)$$

where $v_1 = e\zeta/\mu$ of the first element (often termed the electroosmotic mobility). In many cases the electroosmotic mobility is less than the typical ionic mobility, and, thus, the latter ratio (in the equation immediately above) is often greater than unity and may reach values exceeding 10. For example, taking the ratio of mobilities (in the equation immediately above) to have a value of 2, and matching the flux ratios to within 2% would yield a fractional change in composition of less than 4%. The ratio of mobilities provides an estimate of the slope sensitivity to flux ratio mismatches. The degree of flux ratio matching required in a given application is then directly related to the acceptable tolerance to composition variation in that application. The foregoing provides a basis for designing electroosmotic flow systems in accordance with the invention.

The phenomenon of flux ratio imbalances can also be illustrated using the concept of charge ratio, which is a useful concept for characterizing electrokinetic phenomena. The charge-ratio is defined as the wetted-volume equivalent concentration of surface charge divided by the ionic strength concentration of the bulk fluid. This charge-ratio takes a sign opposite to that of the zeta potential and the magnitude scales linearly with the Debye length, inversely with the pore diameter and super-linearly with the zeta potential.

A finite value of the zeta potential is produced by a finite net charge density on a surface in contact with a fluid. A macroscopic volume enclosing a representative sample of the surface and the fluid must remain charge neutral. Thus the presence of some amount of net charge on the surface requires an excess (deficit) of oppositely-(like-) signed ionic content in the fluid. For a simple equivalent ion pair present in the bulk fluid at concentrations of $c_\pm = c_o$, the concentrations of these same species in an element having a charge-ratio cr is $$c_\pm = c_o(\sqrt{1+cr^2} \pm cr) \tag{12}$$

For a vanishing zeta potential the charge-ratio also vanishes, the concentrations are then the same as in the bulk fluid.

Consider a set of elements arranged in series and carrying a common current, and each having a different value of the charge-ratio. The concentration of positive and negative ions in each element vary in accord with the respective charge-ratios. The current is conserved through the set of elements, however the current will be carried by different fluxes of ions in each element owing to the varying concentrations of ions in each element. The mismatch in ion fluxes between the elements then implies an unsteady mode of operation for portions of, or for the whole system.

Without intending to be bound by any theory, a quantitative expression for the charge ratio may be written based on the Gouy-Chapman theory. Using the Gouy-Chapman theory, the charge-ratio, cr, may be written as:

$$cr = (-8\lambda/\Lambda)\sin h(\epsilon\kappa/2kT) \tag{13}$$

where $\lambda$ is the Debye length in the bulk fluid, $\Lambda$ is the dynamic pore scale that becomes the hydraulic diameter for a right regular conduit, and $\zeta$ is the zeta potential.

Note that the Debye length scales inversely as the square-root of the fluid ionic strength and that the zeta potential also bears a known dependence on fluid ionic strength. Thus, fixing the fluid ionic strength, zeta potential and pore diameter fixes the value of cr.

Two operating regimes are delimited:

1. Elements operating at magnitudes of the charge-ratio less than 0.1 and preferably less than 0.01: Current-driven transport of ions scales directly with the respective bulk-fluid ion mobilities throughout the flow system. In this limit, evolution of electrolyte composition is limited to that occurring in the electrode-containing terminal reservoirs. To minimize contamination of the flow system, it is common in the art to either increase the size of the terminal reservoirs and thus try to 'dilute' the evolution, or; to use bridged reservoirs and thus try to isolate the working fluid from the electrode-bearing reservoir fluid.

2. Elements having an effective surface charge concentration that is a substantial portion, or of the same order of magnitude or greater than the ionic concentration of the fluid (i.e. magnitudes of the charge-ratio greater than about 0.1): Current-driven charge transport of ions in the surface net-charge layers is a significant or even a major fraction of the total charge transfer. In the bulk fluid, charge neutrality is enforced by equal amounts of positive and negative ions, and the fraction of the current carried by any given ion type is according to the mobility of that ion type. On the other hand, the net charge layer contains an excess amount of ions of one sign and a deficit amount of ions of the other sign, and as a result the fraction of current carried by any given ion type is according both to the mobility and the excess or deficit of that ion type.

For example, consider aqueous KCl where the mobilities of the K- and Cl-ions are near equal. In a conduit where the charge-ratio is negligibly small, the current is carried by near equal and opposite fluxes of K and Cl, whereas, in a conduit where the charge ratio is a positive 0.2, the concentration of K is enhanced by a factor of about 1.2 and the concentration of Cl is decreased by a factor of about 0.8, in which case 60% and 40% of the current is carried by fluxes of K- and Cl-ions, respectively.

This phenomenon leads to a mismatch in ion fluxes between elements of an electroosmotic flow system having unequal values of the charge-ratio. For example, a mismatch in ion fluxes may occur at any interface between elements having different pore diameters or zeta potentials or at the interface between any element having a finite charge-ratio and bulk fluid. For slight mismatches (specifically charge ratio mismatches of a few percent or less) the system will likely operate in a stable fashion but larger mismatches can cause several undesirable problems. For example, with large ion flux mismatches the system will be unstable and exhibit unsteady or even oscillatory current and flowrate. Concentration variations through the system, induced by a flux mismatch, can cause dramatic changes in the electrokinetic performance. Such variations are particularly problematic when the electroosmotic device or system is used for chemical analysis, where specific fluid composition is critical, because they degrade analytical performance.

As noted earlier, the problems associated with ion flux mismatches between elements have not affected most of the prior art electroosmotic flow systems largely because the prior art systems are predominantly negligible charge-ratio systems, which implies that the charge ratios of all the elements of the system are equal to each other (namely, zero). However, unmatched ion fluxes become critical in microfluidic systems employing extremely small reservoir and connection volumes, or in such systems employing fine-pored materials, particularly for electrokinetic pressure generation or for bridges where the EOF elements have finite values of the charge ratio. Such imbalances lead to instabilities and unsteady behavior.

Figure 2:
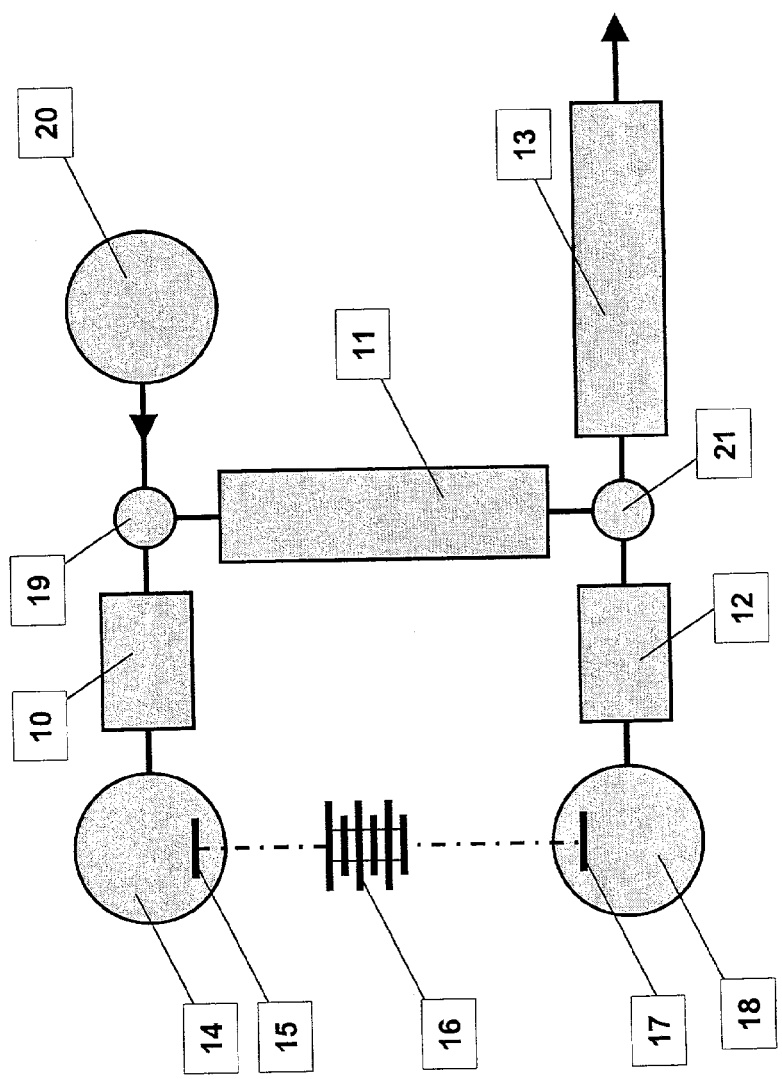
FIG. 2 is a schematic of a three element electrokinetic flow system.

The unsteady behavior due to an imbalance in flux ratios can be illustrated using three case studies for the electroosmotic flow system shown in FIG. 2, which is a three EOF element electroosmotic flow system. As can be seen from FIG. 2, the three EOF elements, i.e., the first EOF element 10, the second EOF element 11 and the third EOF element 12, are arranged in a series, which is connected to a first electrode reservoir 14 and a second electrode reservoir 18 at the two terminal ends. A potential is applied between first and second electrodes 15, 17, respectively, in these reservoirs using current source 16. The three elements are characterized by their respective zeta potentials and dynamic pores scales. Each of the elements is also characterized by its respective geometry factor, which is the effective cross-section area divided by length and formation factor (a porous media topology descriptor). Assume that the second EOF element 11 operates at a substantial value of the charge-ratio.

An inlet source of working fluid, from a working fluid reservoir 20 (say), is connected at junction 19 between the first and second elements. This fluid is electroosmotically transported through the second element and discharged from the junction between the second and third elements. The discharged fluid flows through a flow element 13, i.e., non-current carrying element that may present some back-pressure to the flow of fluid. The flow element 13 is connected to the second element 11 and the third element 12 at junction 21. The flow element 13 is characterized by a load factor, K, that is the ratio of pressure-driven flow conductance of the flow element to that of the second EOF element. The entire system is saturated with a fluid containing some dissociated and ionized species at some concentration $C_o$.

As a specific example, the fluid is a 5 mM aqueous Na-MES (sodium-morpholinoethanesulfonic acid) buffer at a pH of about 6.5 which gives a value for $R_f$ of about 0.27. The pore size and zeta potential of the second element are 400 nm and positive 75 mV, respectively. The charge-ratio for the second element then has a value of about negative two-tenths. For these conditions the value of the flux-ratio of the second element is about 0.07 (which is different from the bulk fluid value of $R_f$=0.27, a reduction of about 80% due to charge layer effects in the EOF element).

Case 1: The First and Third Elements are Nafion

Nafion is a sulfonated fluoropolymer that is essentially impermeable to flow and is highly selective to transfer of positively charged species. Owing to this selectivity, the flux-ratio for Nafion is essentially unity. The flux-ratio for the second element, as given above, is about 0.07. As a result the current through the first and third elements is almost completely carried by fluxes of positively charge species, whereas the current through the second element is carried by near equal and opposite fluxes of positively and negatively charged species. Obviously there is an imbalance in ion fluxes at the junctions. At the junction between first and second elements: positive ions are supplied through the first element at a rate faster than the rate at which they are removed through the second element, and negative ions are supplied through the second element and not removed through the first element. As a result the ionic concentration in the junction increases systematically with time of operation. The opposite occurs at the junction between the second and third elements, where the concentration decreases systematically with time of operation. The fluid in the junction between first and second elements flows into the second element. The time variation of composition of this fluid imposes a time variation on the flow generating capacity of the second element (e.g. the zeta potential decreases with increasing ionic strength). Such electroosmotic flow instabilities resulting from the coupling of a concentration-dependent zeta potential and reservoir fluid evolution are well-known. See Y. Kobatake and H. Fujita, "Flows through charged membranes, I. Flip-flop current vs voltage relation," *J. Chem. Phys.*, 40 pp. 2212–2218 (1964); and Y. Kobatake and H. Fujita, "Flows through charged membranes, II. Oscillation phenomena," *J. Chem. Phys.*, 40 pp. 2219–2222 (1964). Oscillatory behavior resulting from this process has also been observed in high-pressure electrokinetic pumping systems.

Case 2: The First and Third Elements Substantially Lack Surface Charge

The absence of any surface charge on the first and third elements means a vanishingly small value of the zeta potential and hence a vanishingly small value of the charge ratio. The flux-ratio through the first and third elements then takes the value for the bulk fluid (a value of $R_f$=0.27 for the conditions considered) that is mismatched to that of the second element. The finite positive value of the flux-ratio in the first and third elements means that the current is carried by an excess flux of positive ions. The result is the same as the prior case except that the rate of evolution at the junctions will be slightly slower. It is interesting to consider this same case but with a negative zeta potential on the second element (hence a flux-ratio of 0.43) as given above. Under this condition the second element also exhibits an excess flux of positive ions, however this flux is greater than that in the first and third elements (flux-ratios of 0.27). As a result the concentration in the junction between first and second element decreases with time and the concentration between the second and third elements increases with time. Under this scenario the decreasing concentration in the fluid flowing into the second element drives an increase in zeta potential and Debye length in the second element. Both factors in turn produce an increase in the charge-ratio and, hence the flux-ratio, in the second element, that yields a larger flux-ratio imbalance. The system is inherently unstable.

Case 3: Either Case Above with Large Volume Junctions and Substantial Lengths of Conduit Between the Junctions and the Elements.

Assume that the junction volumes are large enough so that the element-to-element flux-ratio imbalances produce a negligible change in the composition at the junctions. However the elements are connected to the junctions by relatively long sections of empty conduits (having a cross sectional area about equal to that of the elements). Flow in these long conduits is essentially one-dimensional and will be near stagnant for conduits containing the first and third elements in the cases given above. Owing to the mismatch in flux-ratio between the bulk fluid and the second element, a diffusion layer will build up in the conduit on either side of the second element. The layer thickness will grow in time and may actually fill the entire length of the empty portion of the conduit. For a positive zeta potential second element the concentration will then systematically increase (decrease) at the input (output) face. For a negative zeta potential second element the reverse will occur. The rate of growth will increase with the degree of mismatch. The varying concentration in the conduits will alter the zeta potential and the fraction of the supply potential appearing across the second, and thus produce a variation in both current and flowrate. In conduits leading to the Nafion (a larger mismatch) the layer growth-rate will be faster, whereas for the element substantially lacking a surface charge the flux ratio actually matches that of the fluid, thus layer-growth at this interface does not occur. It is worth noting here that long, substantially empty conduits used to interconnect elements or reservoirs represent a significant voltage drop hence a significant performance loss.

The invention is the first to recognize that flux ratio mismatches can severely degrade the performance of electroosmotic flow systems. Flux ratio mismatches can lead to problems such as electroosmotic flow instabilities resulting from the coupling of a concentration-dependent zeta potential and reservoir fluid evolution, oscillatory concentration profiles, etc. Based on this recognition, the invention provides electroosmotic flow systems wherein the flux ratios of the EOF elements are matched, or the difference between flux ratios is equal to a target value. The invention also provides methods for selecting and specifying EOF elements (see infra) for a given fluid so that the flux ratios for the elements are equal to each other, or differ from each other by a target amount.

The basic invention and method applies to an electroosmotic flow system where some element(s) of the system operate at a substantial value of the charge-ratio. Elements having a substantial value of the charge-ratio are termed 'active' elements. It will be appreciated that, in the general case, EOF elements with differing pore sizes and zeta potentials are used in an electroosmotic flow system (e.g. small pore size for support elements, larger pore size and high zeta potential for a pump). In accordance with the invention the solute displacement flux through each EOF element is matched by proper selection of the pore size and zeta potential of the element. This matching is done by selecting media properties that provide a near-equal flux-ratio for each EOF element. There is a large range of possible combinations of pore size and materials that provides for matched EOF elements. (see infra). This matching satisfies a necessary condition for steady operation, being the minimal current-driven element-to-element concentration evolution.

2. Example Systems

The evolution of electrode-containing terminal reservoirs is inherent to the process of converting the electron current in the external circuit to an ionic current in the fluid. To minimize contamination by electrolysis products, the invention also provides for separating electrode reservoirs from working fluid reservoirs using appropriately designed bridge elements and using matched EOF elements for connections to current source/sink reservoirs Finally, to achieve a substantial fraction of the ideal electroosmotic performance for the system (i.e. ideal electroosmotic flowrate or electrokinetically generated pressure) the invention provides for maximizing the fraction of supply voltage dropped across active pumping elements, and minimizing flow losses through active support elements. This is achieved by optimizing the relative geometric factors of the elements and by the proper selection of matched element materials.

These various aspects of the invention are now described with reference to the example systems shown in FIGS. 2–8. As noted above, the three EOF elements of the system shown in FIG. 2 are arranged in a series, which is connected to terminal electrode-containing reservoirs at either end. The second element operates at a substantial value of the charge-ratio. A potential is applied between electrodes in these reservoirs. An inlet source of working fluid, from a working fluid reservoir, is connected at the junction between the first and second elements. This fluid is electroosmotically transported through the second element and discharged from the junction between the second and third elements. The discharged fluid flows through a non-current carrying flow element that may present some backpressure to the flow of fluid.

We again denote the first through fourth elements by the subscripts '1' through '4'. The "ideal" flowrate, i.e., the flowrate that would be obtained if there were no losses, through the fourth element is given by:

$$Q_{pf} = v_2 g_2 \Delta V k_4 / (k_2 + k_4) \quad (14)$$

The quantity $g=A/LF$ is the geometry factor where F is a formation factor (a porous media topology descriptor), and A and L are the physical cross sectional area and the physical length of the element, respectively. Also $k=M\Lambda^2 g/\mu$ where $\Lambda$ is the dynamic pore scale, M is the pore geometry number (a second porous media topology descriptor), and $\mu$ is the liquid dynamic viscosity.

The quantities M, F and $\Lambda$ are mathematically defined and given by Johnson et al. [D. L. Johnson, J. Koplik and R. Dashen, J. Fluid Mech. v176, pp. 379–402 (1987)]. The pore geometry number, M, is dimensionless and quantifies the shape of the pores (round and tortuous versus thin-planar and straight, say). For a wide variety of porous media, ranging from packed fibers to packed beads to sandstones to aggregates to foams, the pore topology number is experimentally and theoretically found to generally range in value between $\frac{1}{32}$ and $\frac{1}{16}$. For a right-regular empty conduit the pore topology number reduces exactly to the hydraulic shape factor (e.g. $\frac{2}{3}$ for parallel plane, unity for circular, about 1.12 for square cross section) divided by 32.

The formation factor, F, is dimensionless and quantifies the type of connectedness and the porosity of the medium. The formation factor may be thought of as equal to the square of the tortuosity divided by the connected porosity of the medium. The formation factor is by definition greater than or equal to unity, taking a unit value for a conduit of any cross sectional shape that does not contain porous material.

The dynamic pore scale, $\Lambda$, has dimensions of length. For a conduit of varying diameter along its length, $\Lambda$ will tend to a value near that of the limiting throat diameter. For a bundle of tubes of varying diameter and arrayed in parallel, $\Lambda$ will tend to a value near that of the largest hydraulic diameter in the bundle. For an empty conduit $\Lambda$ reduces exactly to the hydraulic diameter of the conduit.

It will be appreciated that the quantities M, F and $\Lambda$ form a set that replaces all of the traditional descriptors (e.g. porosity, hydraulic diameter, tortuosity, Darcy permeability) employed to describe flow in porous media and flow in empty conduits. In cases that include electrokinetic effects the problem is additionally specified by the Debye length scale (nominally the thickness of the double layer) and the zeta potential. Mathematically it may be shown that $\Lambda$ is the appropriate length scale to determine the degree of double layer overlap.

Returning to the equation for flow rate, the actual flowrate is less than the ideal flowrate due to several losses, including, voltage drops across the first and third elements; pressure-driven flow through the third element, and; electroosmotic flow through the third element. Including these effects gives the actual flowrate $$Q = Q_{pf}(1-cs)/[(1+2as)(1+b/a(1+K))] \quad (15)$$

Here $a=g_2/g_3$, $b=M_3\Lambda_3^2/M_2\Lambda_2^2$, $c=v_3/v_2$, $K=k_4/k_2$ and $s=\sigma_s/\sigma_4$ where $\sigma$ is an effective fluid conductivity (the bulk fluid conductivity increased by any charge layer effects). The quantity K is the 'load' factor and is the ratio of pressure-driven flow conductance of the fourth element to that of the second element. K takes values ranging from zero for operation under high backpressure, to values much greater than unity for flow into a low backpressure load. The numerator in equation 15 gives the loss due to electroosmotic flow through the third element; the first term in the denominator gives the loss due to voltage drops across the first and third elements; and the latter term in the denominator gives the loss due to pressure-driven flow through the third element. These losses are phenomenologically related and, therefore, in general actions taken to reduce one of these losses may alter other losses. For example, making the geometry factor, g, of the first and third elements large compared to that of the second element yields a small value of a. This makes the effect of voltage drop in the first and third elements smaller, but amplifies the effect of pressure-driven loss through the third element.

The systems pressure performance also departs from the ideal case similarly to its flowrate performance. For the case that the outlet of the downstream flow element is closed off, the flowrate through the load element goes to zero and the maximum (or stall) pressure is obtained. Under ideal conditions this pressure is given by $$P_{mf} = \Delta V v_2 g_2 / k_2 \qquad (16)$$

It can be shown that the same effects that reduce the flowrate performance also reduce the pressure performance. Further, that the stall pressure produced is given by $$P_m = P_{mf} Q / Q_{pf} \qquad (17)$$

with the flowrate ratio (equation 15) taken in the limit of K=0. Thus, a consideration of factors modifying the flowrate performance of the system applies equally towards optimization of the pressure performance of the system. Many electroosmotic flow systems involve high pressure, e.g., electrokinetic pumps. Most of the prior art on bridges has been directed at low pressure applications (i.e. pressure differences of less than a few psi). In such low pressure applications the issues of mechanical strength of the bridge or the means used to retain the bridge are easily satisfied. Therefore, prior art bridge designs are generally not applicable to high pressure systems (i.e. pressure differences of greater than ten and likely greater than several thousands of psi), where issues of mechanical strength and means of retaining the bridges becomes critical.

The foregoing can be used to evaluate the performance of prior art bridges as compared to the ideal case and for high pressure applications.

The polymer plug is essentially impermeable to flow and, therefore, the performance is mainly reduced by the voltage drop across the bridging material. However the ion mobility in such bridges tends to be relatively low compared to that in the fluid, which implies that s<<1. Polymers generally undergo plastic deformation under pressure. Polymer plug materials are generally not suitable for high pressure applications unless the plug is combined with some integral mechanical support.

The solid ionic conductor, similarly to the polymer plug, is essentially impermeable to flow and, therefore, the performance is mainly reduced by the voltage drop across the bridge. The ion mobility in such bridges tends to be relatively high, which implies that s<<1. In many cases the solid ionic conductor is a material like Nafion (a Teflon-based polymer) and the mechanical strength considerations are like that of the polymer plug.

Vanishing bridge zeta potential: The performance is not reduced by electroosmotic losses, but is still reduced by both voltage and pressure losses.

Bridge zeta potential polarity opposite that of the pump element: Performance is reduced by both voltage and pressure losses but actually enhanced by electroosmotic flow. However flux-ratio matching cannot be achieved for any conditions except a negligible charge-ratio.

Bridge pore size about equal to the Debye length and a non-vanishing bridge zeta potential: essentially the same as a solid ionic conductor.

Loose fiber plug or large-pored barrier: Performance may be reduced by all three factors. However, owing to the large pore size, this approach is limited to applications with K>>1.

An example design of bridge elements (for example, the first element) for the system shown in FIG. 2, in accordance with the invention, can now be illustrated. In accordance with a first aspect of the invention, the flux ratio of the first element is matched to that of the second element. Using the conditions given previously, the fluid is a 5 mM aqueous Na-MES buffer at a pH of about 6.5 which gives a value for $R_f$ of about 0.27. The pore size and zeta potential of the second element are 400 nm and positive 75 mV, respectively. The charge-ratio for the second element then has a value of about negative two-tenths. For these conditions the value of the flux-ratio is about 0.07 (which is different from the bulk fluid value of $R_f$=0.27, a reduction of about 80% due to charge layer effects in the EOF element). The load factor is 4 and the pressure is near ambient at the junction between the first and second elements. The flux-ratio through the first element will match that through the second element by selecting a first element pore size of about 40 nm and a first element zeta potential of about positive 10 mV.

It is also preferable to minimize the fraction of voltage drop across the element and reduce but not eliminate electroosmotic flow through the element. This is achieved by selecting the proper geometry. The geometry factor of the first element is selected to be at least ten times that of the second element. Given the material specification and this geometry factor, there will be a flowrate through the first element that is about 5% that through the second element. Finally the voltage drop across the first element will be about 10% of the total supply potential, or less when using a larger geometry ratio.

It is obvious that the devices and methods given in the above example are not limited to the particular choices of materials, working fluid, ionic content in the fluid, pore size, or load factor used in the example. For illustration take the conditions of the example but let the zeta potential of the second element be a negative 75 mV. The flux-ratio has a value of about 0.43. Matched conditions in the first element require a pore size of about 30 nm and a zeta potential of about negative 10 mV.

For another example embodiment, take the conditions of the example but let the ionic components in the fluid be 1 millimolar TRIS-HCI at a pH of about 8.25 (i.e. an $R_f$ value of about negative 0.2). The flux ratio has a value of about negative 0.5. Matched conditions in the first element require a pore size of about 45 nm and a zeta potential of about positive 10 mV.

We can illustrate the effects of mismatched flux ratios on the fluid composition for the system shown in FIG. 2. Focusing on the second, third and fourth elements, as noted earlier, the elements have a common junction. Current is carried by the second and third elements, flow is from the second into the third and fourth elements. The concentration at the common junction and, hence, the concentration of the fluid flowing into the fourth element (its inlet concentration), which is possibly different from the inlet concentration of the second element, is given by:

$$\frac{C_4 - C_2}{C_2} = \frac{n_2}{v_2(1 - 1/(1+K))}(R_2 - R_3) \qquad (18)$$

where $C_4$ and $C_2$ are the inlet concentrations for the fourth and second elements, respectively. Here v and n are the effective electroosmotic mobility and summed effective ion mobility, respectively (the term 'effective' implies that the quantities are modified from the bulk values by any charge layer effects). K is the load factor, which, for the given example, is equal to the ratio of pressure-driven flow through the fourth element to that through the second element as a result of any pressure at the common junction. The term $R_n$ represents the flux-ratio through the $n^{th}$ element.

In the limit of negligible charge layer effects (i.e. negligibly small charge-ratio), the values of v and n take the ideal or bulk values, and the value of the flux ratio becomes equal to the relative difference in bulk fluid ion mobilities (here this relative difference, denoted by the symbol $R_f$, is defined as the positive less the negative ion bulk fluid mobilities divided by their sum). The magnitude of $R_f$ is by definition less than or equal to unity going to zero for equimobile ion pairs.

For reference: The value of $R_f$ for several common ionic solutions and buffers is about: 0.78, 0.27, 0.1, 0.05, −0.02, −0.2, −0.45 for TFA, Na-MES, Na-acetate, Na-borate, KCl, NaCl, TRIS-Cl, respectively.

The lead term on the right-hand-side of equation 18 is the ratio of the current per unit concentration to the flowrate, which represents the slope sensitivity to flux imbalances driven by the difference in R-values of the elements. This lead term may be of either sign and the magnitude generally has a value of about 2 (but may range between values of about 0.2 to values of about 20). Thus, to maintain the integrity of fluid composition, say, to within ±10%, the difference in R-values must be kept, say, less than ±5% and preferably lower. Note that for finite values of the load factor K, pressure is generated at the common node and this increases the magnitude of the lead term in equation 18. Thus, the sensitivity to flux-ratio mismatches is greater in high pressure electrokinetic pumping applications.

The source of ionic strength and pH evolution is net concentration transport. Thus steady operation requires a suitably small value for the difference in R-values given in equation 18. The R-value for a given element may be written as $R=R_f+\Delta R$ where $R_f$ is the relative difference in bulk ion mobilities and $\Delta R$ is the variation due to charge layer effects (a nonlinear function of zeta potential, fluid composition and pore size). For negative values of the zeta potential the charge-ratio is positive and $0 \leq \Delta R \leq 1-R_f$ approaching the upper limit as the charge-ratio becomes large. For positive values of the zeta potential the charge-ratio is negative and $-(1+R_f) \leq \Delta R \leq 0$ approaching the lower limit as the magnitude of the charge ratio becomes large.

For reference: Taking the value of R=0.2, the relative difference between R and $\Delta R$ (i.e. $\Delta R/R-1$) is about −12, −3.6, −1.3, −0.6 percent for a pore diameter of 1000 times the Debye length and zeta potentials of 75, 37.5, 15 and 7.5 mV, respectively, or the relative difference is about −59, −19, −6.3 and −3.1 percent for a pore diameter of 200 times the Debye length and same set of zeta potentials, respectively, or it is about −96, −32, −11 and −5 percent for a pore diameter of 100 times the Debye length and same set of zeta potentials, respectively.

A like analysis can be applied to a pair of electroosmotic flow elements connected fluidically and electrically in series or to a complex network of interconnected elements. Each of the elements may carry a different amount of flow and current compared to the other elements and even a fluid of different composition. The general rule is that the net solute flux between electrically connected elements must be matched to achieve steady operation.

As a second example, consider the flow control device described by Paul, Arnold and Bailey in U.S. Patent Publication No. 2002/0189947, incorporated by reference herein. The present invention may be applied to their device by: taking the electrode reservoirs, power supply and electrodes, and the first, second and third elements of FIG. 2; taking an externally applied pressure-driven flow to be supplied into the junction between the first and second elements of FIG. 2 (that is replacing the working fluid reservoir of FIG. 2), and; taking the flow element of FIG. 2 to be replaced by an outlet working fluid reservoir. The present invention may then be directly applied to replace the EOF element set employed in all of the variations recited by Paul, Arnold and Bailey, with the attendant benefit of providing stable operation. Because this involves changing the pressure at various junctions, the structure of the junctions would have to be changed accordingly.

Figure 6:
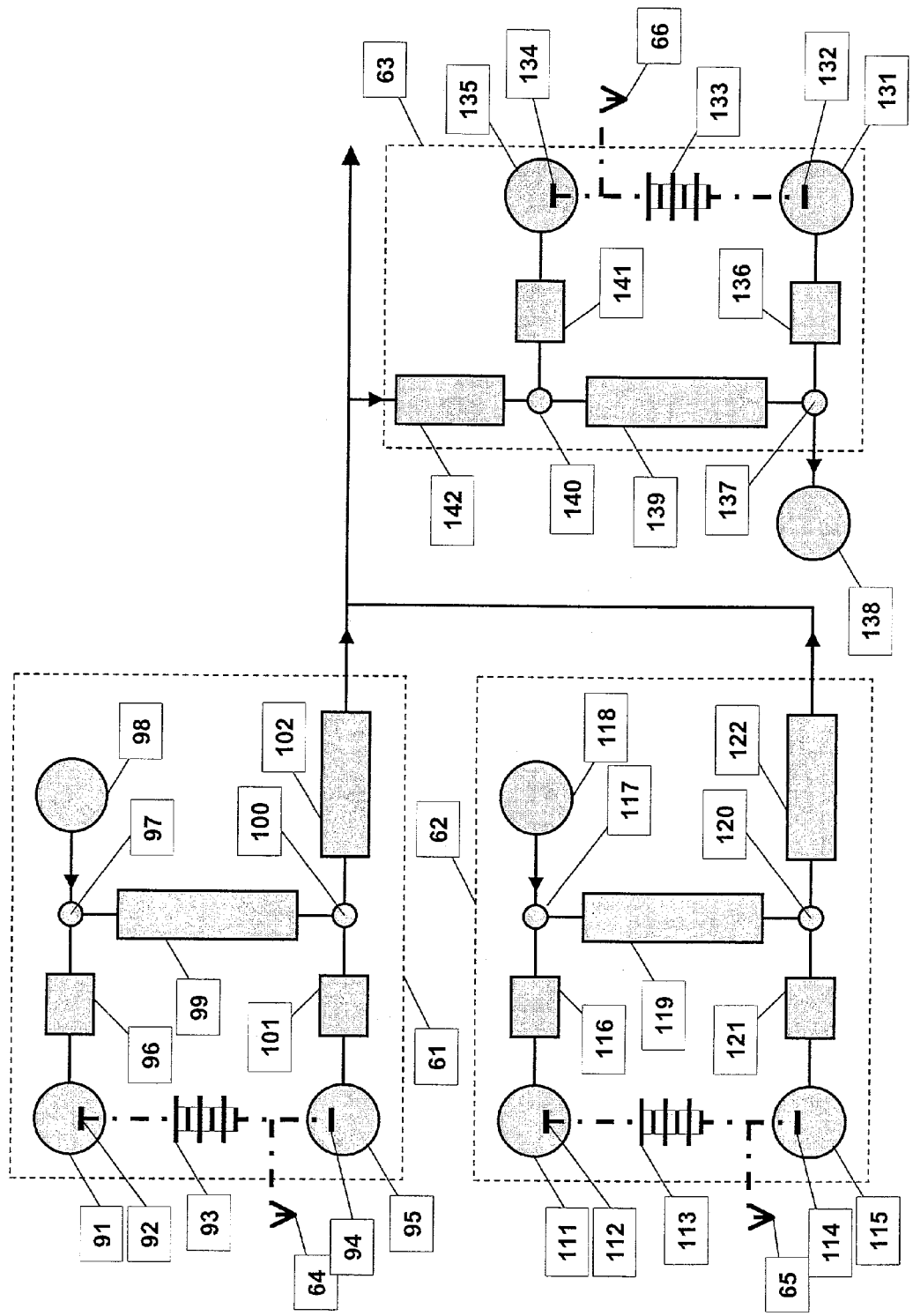
FIG. 6 is a schematic of a multiple EOF element electrokinetic flow system.
Figure 7:
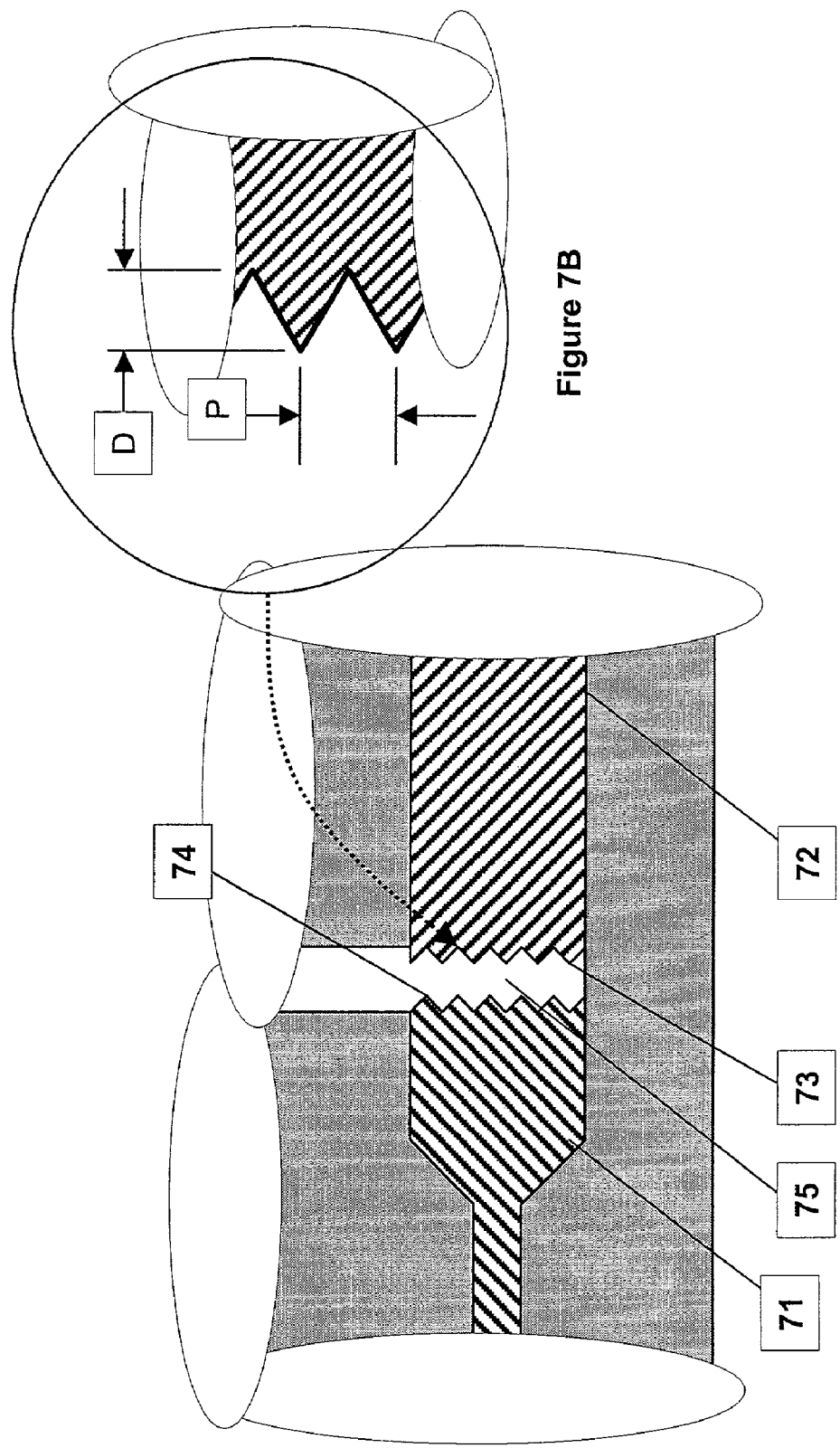
FIG. 7A is a schematic of a serrated interface with FIG. 7B showing a detail of the serrations of the surface.

As another example embodiment consider the design of a multi-active-element electroosmotic flow system shown schematically in FIG. 6. FIG. 6 shows three separately powered sub-systems 61, 62 and 63 providing flows of two different fluids to a common node and thence to a common load. Sub-system 63 is a version of the electroosmotic flow control device (see supra) operated in a shunt-type mode. Preferably, subsystems 61, 62 and 63 should be connected in such a way that the lower potential electrodes for the three power supplies (or the higher potential electrode for the three power supplies) are at a common potential called the system common. This prevents current flow from one subsystem to another. For example, the electrodes could be connected to the earth. FIG. 6 shows that the lower potential electrodes are connected to the system ground at 64, 65 and 66 for sub-systems 61, 62 and 63, respectively.

The subsystems shown in FIG. 6 are essentially the same as the system shown in FIG. 2. Thus, subsystem 61 is a three EOF element electroosmotic flow system. As can be seen from FIG. 6, the three EOF elements, i.e., the first EOF element 96, the second EOF element 99 and the third EOF element 101, are arranged in a series, which is connected to a first electrode reservoir 91 and a second electrode reservoir 95 at the two terminal ends. A potential is applied between first and second electrodes 92 and 94, respectively, in these reservoirs using current source 93. The three elements are characterized by their respective zeta potentials and dynamic pore scales. Each of the elements is also characterized by its respective geometry factor, which is the effective cross-section area divided by length and formation factor (a porous media topology descriptor). An inlet source of working fluid, from a working fluid reservoir 98, is connected at junction 97 between the first and second elements. This fluid is electroosmotically transported through the second element and discharged from the junction between the second and third elements. The discharged fluid flows through a flow element 102, i.e., a non-current carrying element that may present some backpressure to the flow of fluid. The flow element 102 is connected to the second element 99 and the third element 101 at junction 100. The flow element 102 is characterized by a load factor, K, that is the ratio of pressure-driven flow conductance of the flow element to that of the second EOF element. The entire system is saturated with a fluid containing some dissociated and ionized species at a some concentration $C_{o1}$.

Subsystem 62 is also a three EOF element electroosmotic flow system. As can be seen from FIG. 6, the three EOF elements, i.e., the first EOF element 116, the second EOF element 119 and the third EOF element 121, are arranged in a series, which is connected to a first electrode reservoir 111 and a second electrode reservoir 115 at the two terminal ends. A potential is applied between first and second electrodes 112 and 114, respectively, in these reservoirs using current source 113. The three elements are characterized by their respective zeta potentials and dynamic pores scales. Each of the elements is also characterized by its respective geometry factor, which is the effective cross-section area divided by length and formation factor. An inlet source of a second working fluid, from a working fluid reservoir 118, is connected at junction 117 between the first and second elements. This fluid is electroosmotically transported through the second element and discharged from the junction between the second and third elements. The discharged fluid flows through a flow element 122, i.e., a non-current carrying element that may present some backpressure to the flow of fluid. The flow element 122 is connected to the second element 119 and the third element 121 at junction 120. The flow element 122 is characterized by a load factor, K, that is the ratio of pressure-driven flow conductance of the flow element to that of the second EOF element. The entire system is saturated with a fluid containing some dissociated and ionized species at a some concentration $C_{o2}$.

Similarly, subsystem 63 is also a three EOF element electroosmotic flow system. As can be seen from FIG. 6, the three EOF elements, i.e., the first EOF element 136, the second EOF element 139 and the third EOF element 141, are arranged in a series, which is connected to a first electrode reservoir 131 and a second electrode reservoir 135 at the two terminal ends. A potential is applied between first and second electrodes 132 and 134, respectively, in these reservoirs using current source 133. The three elements are characterized by their respective zeta potentials and dynamic pores scales. Each of the elements is also characterized by its respective geometry factor, which is the effective cross-section area divided by length and formation factor. Liquid enters subsystem 63 through a flow element 142, i.e. a non-current carrying element that may present some pressure drop to the flow of liquid. The flow element 142 is connected to the second element 139 and the third element 141 at junction 140. The flow element 142 is characterized by a load factor, K, that is the ratio of pressure driven flow conductance of the flow element to that of the second EOF element. Liquid is electroosmotically and possibly pressure-driven through the second element and discharged at the junction 137 between first and second elements to outlet reservoir 138. The entire system is saturated with a fluid containing some dissociated and ionized species at a some concentration $C_{O3}$.

The current path(s) determine which elements are active and which sets of elements need to be matched. In FIG. 6 three separate power supplies provide separate current loops in the three sub-systems. The EOF elements in each sub-system need to be matched, but the EOF elements of one sub-system do not need to be matched to those in the other sub-system. Thus the same considerations, devices and methods applied to the system of FIG. 2 apply equally here to each sub-system. Obviously, additional fluid-sourcing sub-systems may be added. Likewise additional sub-systems can be added as fluid sinks either in a series or shunt fashion. The three-element system of FIG. 2 can serve as the 'building-block' unit for more complex electroosmotically-driven flow systems.

3. Novel Junctions and Terminal Portions

In a second aspect, the invention provides for novel designs for and methods of designing certain sections, called junctions, of an electroosmotic flow system, such as sections that are relatively empty conduits or sections at the ends of or between EOF elements or bridge elements. If the charge-ratio of these sections is negligible, the likely case, there will be a displacement flux mismatch at the interface between such a section and the element. A concentration/diffusion layer forms at such an interface, which adversely affects performance. The invention provides for electroosmotic flow systems in which the thickness of the concentration/diffusion layer at the interfaces with the junction fluid is minimized. Several approaches are available for minimizing the thickness of the diffusion layer including, without limitation, the following:

1. The cross-sectional area of the element/interface is substantially increased (area as compared to the limiting cross-sectional area of the EOF element).
2. The pore size and zeta potential of the element are selected, still consistent with I above, to provide some finite flow through the element.
3. The physical layout of the interface is done in a fashion so as to promote flow past the face of the EOF element. This entails minimizing the separation between the faces of the elements.

The diffusion layer that forms at the interface between an EOF element and junction fluid is analogous to the diffusion layer that forms at the interface between a current-carrying electrode and a fluid. See for example J. O'M. Bockris and A. K. N. Reddy, Modem Electrochemistry V2, (Plenum N.Y., 1970), pp. 1055–1060, which is incorporated by reference herein.

A junction of an electroosmotic flow system is defined as that part or component of the electroosmotic flow system at which one element (which can be an EOF element, bridge element or a flow element) of the electroosmotic flow system is in fluidic and/or electrical communication with one or more other elements (which can be EOF elements, bridge elements or flow elements) or reservoirs.

As noted above, each EOF element has an inlet portion and an outlet portion. The inlet and outlet portions of an element are usually, but not always, located at the terminal ends of the element and, therefore, are also referred to herein as terminal portions. The inlet and outlet portions essentially comprise surfaces through which the fluid and current enter and exit the element. In several embodiments, these surfaces are planar and perpendicular to the flow axis, e.g. the inlet and outlet faces of a right-regular conduit. However, it is not necessary that these surfaces always be planar. For example consider a cylindrical conduit that contains porous media, a finite length of this porous media may protrude beyond the walls of the conduit, implying that a portion of the end face surface is planar and a portion is cylindrical.

Based on the foregoing a junction is comprised of a terminal portion of an element (i.e., an EOF element, a bridge element or a flow element) and the terminal portion of one or more other elements (i.e., EOF elements, bridge elements or flow elements) and/or one or more reservoirs. Further, because elements or reservoirs are in fluidic and electrical communication at the junction, the junction contains a fluid, e.g., the working fluid. The fluid contained in the junction is henceforth referred to as the junction fluid.

The invention is based on the discovery that the diffusion layer formed at an interface between the terminal portion of an element and the junction fluid affects the performance of an electroosmotic flow element and the system. Therefore the invention provides designs and methods for minimizing diffusion layer effects.

For an electroosmotic flow element carrying a current I, the average current flux through the element, denoted as the element current flux, is $J=I/A$, where A is the effective cross-section area of the element (defined supra). Owing to variations in geometry and electric fields with a junction there will be a distribution of normally directed current flux, $J_t$, over the surface area of the terminal portion of an element. Further the distribution $J_t$ will have some maximum value(s) $J_{t,max}$. In accordance with the invention, the terminal portion of the electroosmotic flow element is designed so that $J>J_{t,max}$ and more preferably $J\gg J_{t,max}$. To this end variations in $J_t$ arising from any microscopic irregularities, being features having length scales less than about 500 Debye lengths or less than about five dynamic pore scales, are treated as smooth As is evident, the terminal current flux can be reduced relative to the element current flux by increasing the surface area of the terminal portion relative to the effective cross-section area. In preferred embodiments the surface area of the terminal portion is 50% greater than the effective cross-section area of the element. In yet another embodiment, the surface area of the terminal portion is 100% greater than the effective cross-section area of the element and in yet other embodiment, the surface area of the terminal portion is 200% greater than the effective cross-section area of the element.

FIG. 3A and FIG. 3B show section and plan views, respectively, of a possible layout for the junction between two elements, a first element 30 and a second element 31, for example, in a chip microflow device. The first element is connected to an electrode reservoir 33 having an electrode 34, which implies that the first element is a bridge element. The second element is connected to a working fluid reservoir 32 at junction 35. In the general case, the first element may be an EOF element connected to another EOF element at a junction or the second element may be bridge element connected to an electrode reservoir. Thus, the design features described below are equally applicable to a junction between two (or more) EOF elements or between one (or more) EOF element and a bridge element.

Several features of the invention are illustrated: 1) The ends of the first and second elements are extended well into the reservoir 32 to minimize the effects of diffusion layers at the interface between the EOF element and the junction fluid. 2) The end of the second element is flared to increase the surface area of the face 36 of element 31 and also brought into close proximity to the face 37 of the first element. 3) The thickness of the first element is also increased to increase cross sectional area and thus reduce first element voltage drop.

Figure 4:
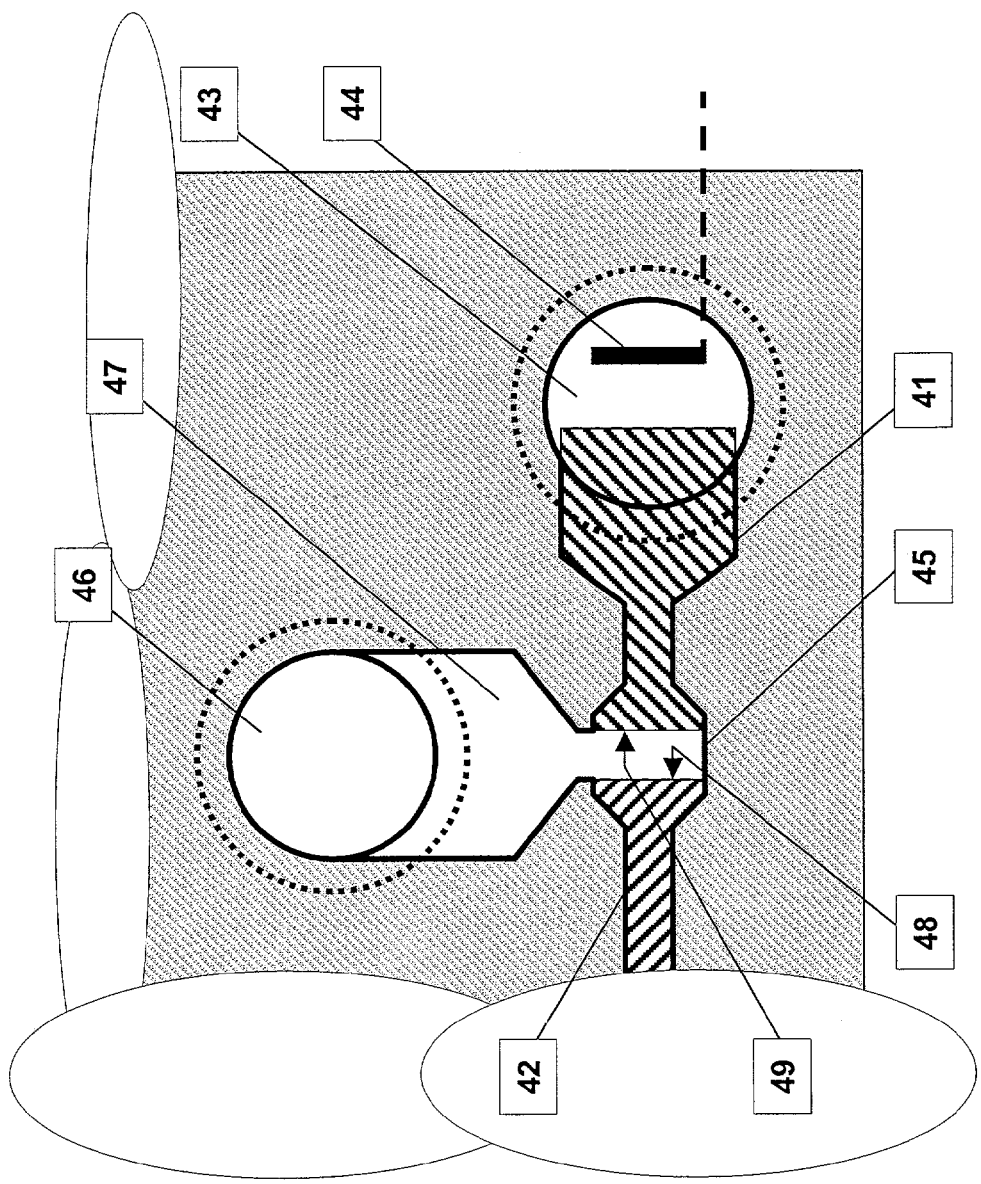
FIG. 4 is a plan view of a possible EOF element microconduit junction, connected to a working fluid reservoir.

FIG. 4 is a plan view of an alternative possible layout for the junction between a first EOF element 41, which is shown as a bridge element, and a second EOF element 42, for example, in a chip microfluid device. The features of the invention noted above are also included in this device. Thus, element 41 is connected to electrode reservoir 43, which contains electrode 44. Terminal faces 49 and 48 of the elements 41 and 42 are connected to junction 45, which is also connected to working fluid reservoir 46 through flow element 47. The flow element 47 is an empty conduit and is preferably of sufficient depth and width and short enough so that the pressure drop through it is negligible. As can be seen, in accordance with the invention, the area of faces 48 and 49 is considerably larger than the effective cross-section area of the elements to minimize the thickness of the diffusion layers that form at the interfaces between the faces 48 and 49 and the junction fluid in the junction 45.

Figures 5A, 5B:
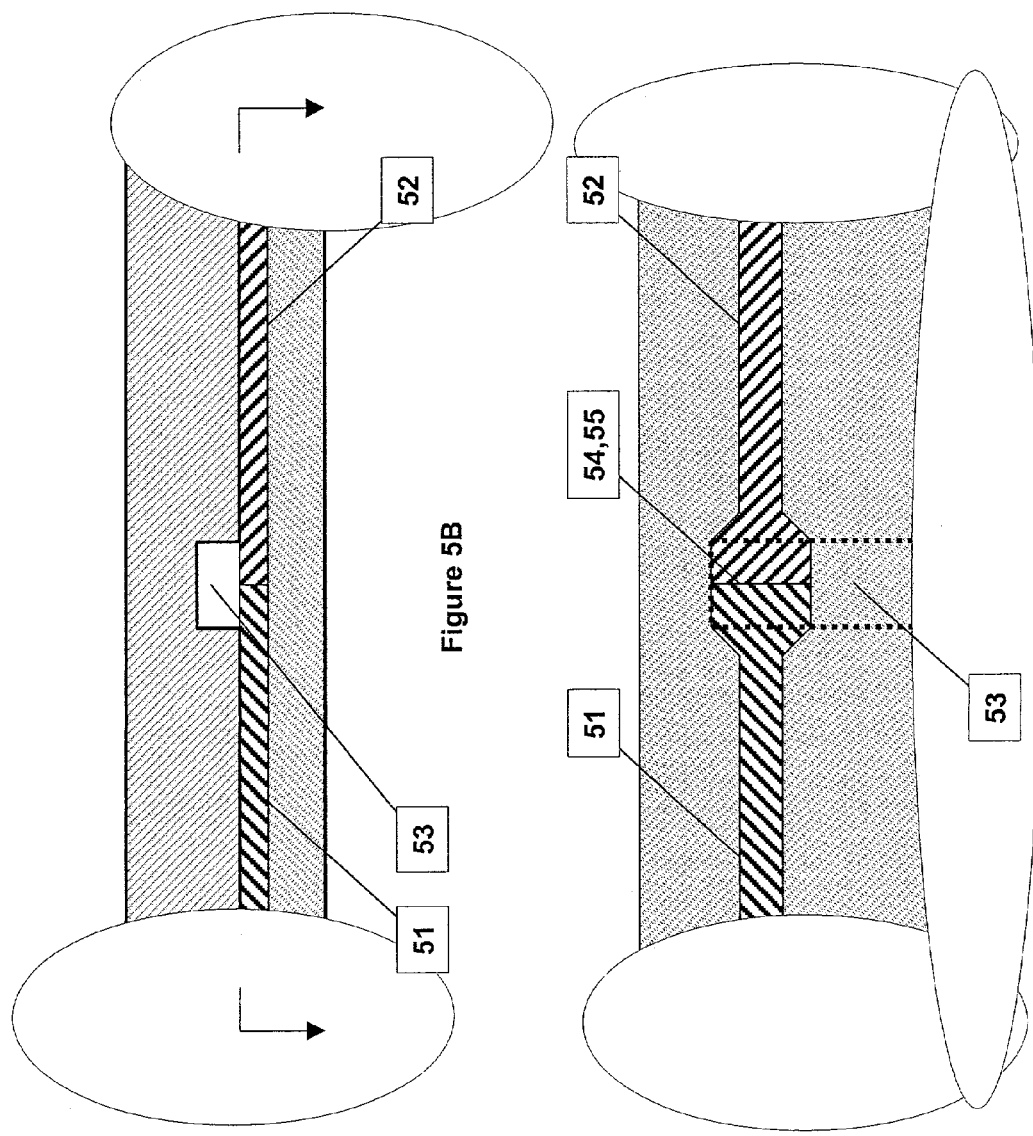
FIGS. 5A and 5B are section and plan views of a possible EOF element microconduit junction, using a multilayer construction.

Another embodiment of the invention is shown in FIGS. 5A and 5B, which show plan and section views, respectively, of another type of a junction that might be used, for example, in a chip microflow device. In this case two EOF elements 51 and 52 are in direct contact at their respective faces 54 and 55 and in one plane of the device. When faces 54 and 55 are in direct contact with each other, the volume of bulk liquid enclosed by the faces is minimized. A flow element 53 is in a second plane of the device and intersects the junction of the first and second elements. This junction layout may be used as an alternative to those shown in FIGS. 4 and 5. It is obvious that the junction geometry of FIG. 5 can be extended to elements and conduits in multiple different planes.

Figure 3:
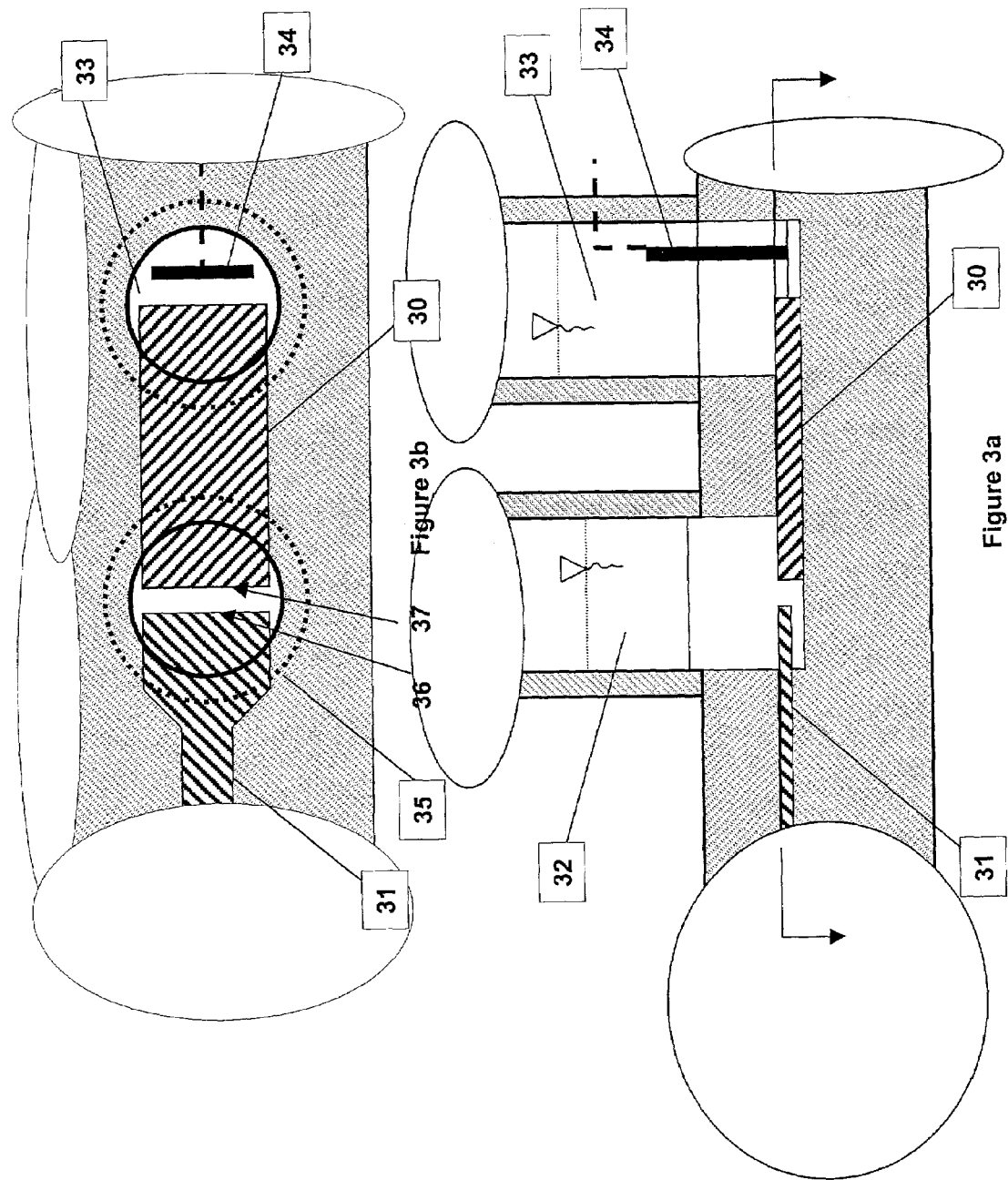
FIGS. 3A and 3B are section and plan views of a possible EOF element junction made at a working fluid reservoir.

In FIGS. 3 through 5 the ends of elements have been flared to provide an increased surface area for the interfaces between the faces of the elements that are in contact with junction liquid at a junction. Thus, in accordance with the invention, the surface area of the terminal face of an EOF element (or a bridge element) is made much larger than the effective cross section area of the element. For example, FIG. 4 shows a case where the element is tapered from an intermediate cross-section at the microconduit junction (done to minimize diffusion layer thickness), to a smaller cross section in the middle (done to provide mechanical strength and meet geometry factor requirements) to a large cross section at the bridge reservoir junction (done to minimize diffusion layer thickness). A similar approach is employed as needed to meet the required relative geometry factors.

FIGS. 3 to 5 show terminal faces that are planar. If the face is kept planar, the dimensions of the face must be increased to increase the surface area of the face as is shown in FIGS. 3–5. An alternative to this approach is make the face non-planar. Thus, if the face is made jagged, it will have a larger surface area compared to a planar face with similar dimensions. For example, an approach to increasing the cross sectional area is to make the surface in the form of sawteeth, i.e., a serrated surface. The serrations may be regular or irregular and may have any shape (including a ragged or torn edge). The use of a serrated surface is shown in FIGS. 7A and 7B. FIG. 7A shows EOF elements 71 and 72 having serrated faces 73 and 74. Both faces are connected to junction 75. FIG. 7B is a blow-up of the serrations showing the pitch P and depth D of the serrations. It is preferable that the aspect ratio of the serrations (defined as the depth divided by the pitch of the serrations) is between about ¼ and 2. Aspect ratios less than about ¼ add limited value and aspect ratios greater than about 4 may be less effective than values less than about 4.

Another method to minimize the effects of diffusion layers is to employ a graded junction. The simplest graded junction employs a first flow material (the flow element having a first charge ratio) that is butt- or lap-joined to a second porous material (having a second charge ratio), which is in contact with the junction liquid. The second porous material is selected to have a charge ratio that has the same sign as that of the first material and has a value that is between that of the first material and that of the junction liquid (the charge ratio of the junction liquid being zero by definition). Preferably the value of the second charge ratio is about one-half that of the first charge ratio (to be effective, a value between about ¼ and ¾ of the first charge ratio). Obviously this may be extended to more than two materials in series and even to a single material that has a continuously graded value of the charge ratio. From the definition of the charge ratio it is obvious that graded values of the charge ratio may be realized by using materials having different amount of surface charge or having different dynamic pore scales.

Figure 8:
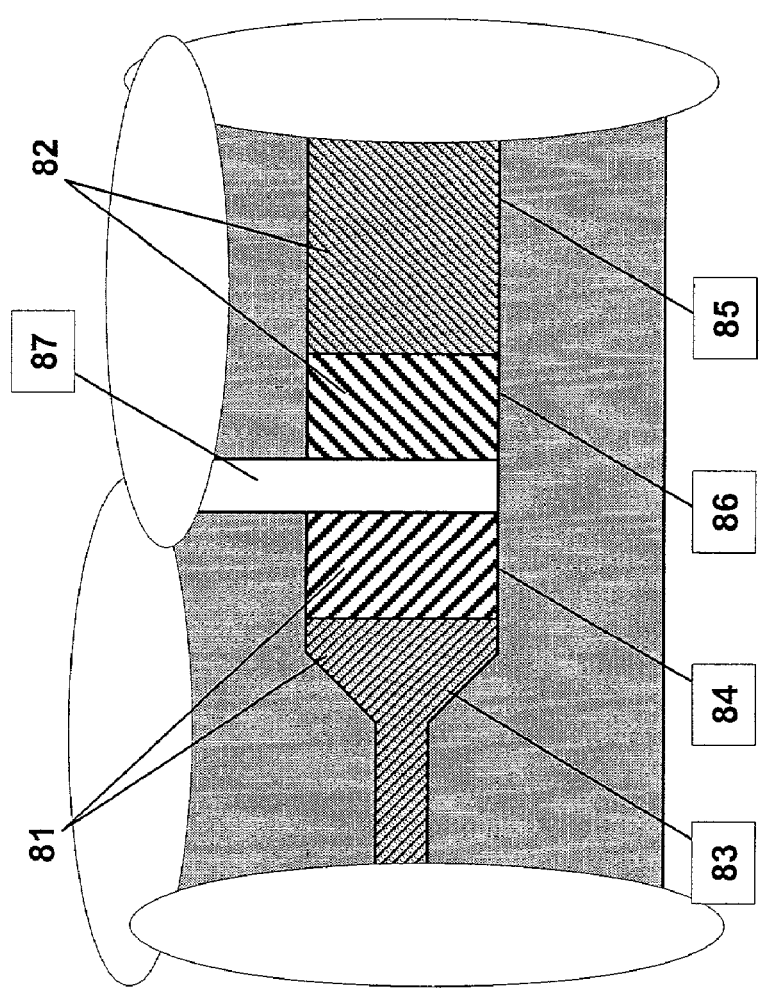
FIG. 8 is a schematic of an electroosmotic flow element using graded materials.

The use of a graded junction is illustrated in FIG. 8, which shows graded EOF elements 81 and 82 that terminate injunction 87. Element 81 is made of materials 83 and 84 and element and element 82 is made of materials 85 and 86.

Another method to minimize diffusion layers is to arrange the elements so that there is flow through the region of diffusion layer formation. This can be accomplished by providing some flow (electroosmotic or pressure driven) through the element face. For elements with very low flow through them (e.g. many bridge elements), arrangements which provide flow past the surface of the element is preferred. FIGS. 3, 4, 7, and 8 all are arranged so that flow through the junction passes over the ends of the EOF elements and therefore will help minimize diffusion layer growth. An additional configuration to promote flow past the end of an element is shown in FIG. 9.

Figure 9:
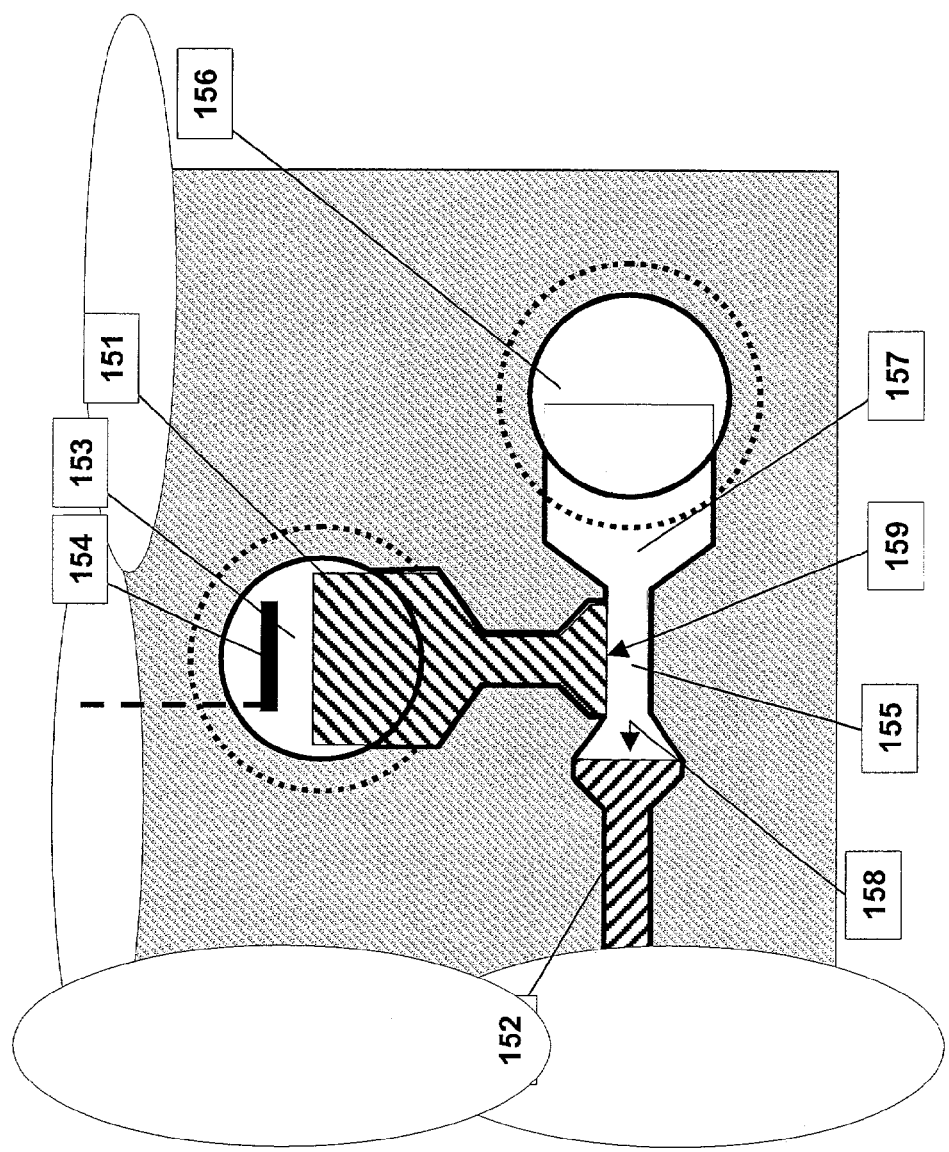
FIG. 9 is a plan view of possible EOF element microconduit junction, connected to a working fluid reservoir.

FIG. 9 is a plan view of an alternative possible layout for the junction between a first EOF element 151, which is shown as a bridge element, and a second EOF element 152, for example, in a chip microfluid device. The features of the invention noted above are also included in this device. Element 151 is connected to electrode reservoir 153, which contains electrode 154. Terminal faces 159 and 158 of the elements 151 and 152 are connected to junction 155, which is also connected to working fluid reservoir 156 through flow element 157. The flow element 157 is an empty conduit and is preferably of sufficient depth and width and short enough so that the pressure drop through it is negligible. In accordance with the description given above, element 151 is positioned so that its face 159 is swept by fluid flowing between EOF element 152 and the flow element 157 connected to the reservoir. In other words, the direction of the flow streamline of the fluid flowing through the junction 155 has a substantial component that is tangential to the face 159 of EOF element 151. In configurations where the faces of the two elements are not parallel to one another, one must avoid arrangements that cause too large an increase in the local current density through the face (and therefore increase the diffusion layer), as this may offset the reductions due to the flow arrangement.

Obviously the various methods of minimizing diffusion layer effects can be used alone or in combination. Thus, methods of increasing cross sectional area, e.g. increasing the size of planar faces or using non-planar faces, using a gradation, and increasing flow past the surface may be used alone on in combinations. The layouts shown in FIGS. 3–5 and 7–9 illustrate specific types of junctions. The methods may be equally applied to all of the other types of junctions between elements and junction liquid.

One may also use inhomogeneous or layered or stacked media for structural integrity or ease of manufacturing. One example is the use of asymmetric porous media. As a further example, one may use a section of fine-pored material to provide a finite value of the charge ratio where this material exhibits limited structural integrity or strength. This fine-pored material may be backed by a larger pored material that maintains the charge ratio but allows greater structural integrity with minimal performance loss. This configuration is more likely to be a composite of different materials than a single material with graded properties.

The devices and methods are not restricted to planar elements. It is obvious that the same issues of substantial charge-ratio and the need to match flux-ratios to obtain stable operation applies to any electroosmotic flow system. The EOF element may equally be discrete components (e.g. porous-media filled or packed capillaries) coupled together using some type of discrete connector (e.g. miniature HPLC fittings). Or equally the system may be some combination of planar chip and discrete components.

Additional details on implementing the designs and methods of the invention are provided below.

4. General Design Considerations

A method to select an appropriate matched material is outlined below. The method can be applied equally to selection of elements of a whole system.

The material, pore size and geometry of a bridge is selected to about equally minimize:

1. The fraction of the total flowrate that is carried as pressure-driven flow through the elements. Preferably some finite flow is provided to control the thickness of diffusion layers.

2. The fraction of the total flow that is carried as electroosmotically-driven flow through the elements. Preferably some finite flow is provided to control the thickness of diffusion layers.

3. The fraction of the total potential applied that appears across the elements.

The selection of material and pore size is further conditioned to match the displacement flux through the other EOF elements in the system.

A suitable procedure must be used to reduce these goals to material and geometry specifications. One possible procedure, for cases with a load factor (K) of order unity, follows:

The problem is generally specified in terms of the transport fluid type and composition, target ideal pressure and flowrate. These yield specifications for the pumping element material, physical geometry and porous media properties. Then referring to equation 15:

1. Select some small number $\epsilon$, where the fraction of flowrate performance will be better than about $1-3\epsilon$.

2. The ratio $\Lambda_{1,3}/\Lambda_2$ is selected less than $\epsilon\sqrt{(1+K)}$ 3. The value of $\zeta_{1,3}$ is selected to make the value of $\zeta_{1,3}\sigma_{1,3}/\zeta_2\sigma_2$ about $\epsilon$.

4. The value of $\Lambda_{1,3}$ is refined, still consistent with step (2) and that may also require a new attendant value of $\zeta_{1,3}$ to satisfy step (3), that provides a minimal and preferably negligibly small difference in displacement fluxes through the system (i.e. minimize the value of $R_2-R_{1,3}$). A range of solutions maybe found and selected from based on the materials available.

5. The geometry ratio $g_2/g_{1,3}$ is selected to be about $\epsilon$.

One possible procedure, for cases with large values of the load factor (K), follows:

1. Select some small number $\epsilon$, where the flowrate performance will then be better than about $1-3\epsilon$.

2. The ratio $\Lambda_{1,3}/\Lambda_2$ is selected less than unity.

3. The value of $\zeta_{1,3}$ is selected to make the value of $\zeta_{1,3}\sigma_{1,3}/\zeta_2\sigma_2$ about $\epsilon$.

4. The value of $\Lambda_{1,3}$ is refined, still consistent with step (2) and that may also require a new attendant value of $\zeta_{1,3}$ to satisfy step (3), that provides a minimal and preferably negligibly small difference in displacement fluxes through the system (i.e. minimize the value of $R_2-R_{1,3}$). A range of solutions may be found and selected from based on the materials available.

5. The geometry ratio $g_2/g_{1,3}$ is selected to be less than c, and preferably as small as practical.

Given the physics and development of the problem recited above and the statement of goals given here, these procedures are obviously one of many that could be equally used to determine the material specifics.

It will be appreciated that like procedures can be applied to multiple electroosmotic elements joined in a variety of series and parallel configurations.

Materials

The requirement is for sets of materials that provide matched charge-transfer properties. As noted above a material can be characterized by a charge-ratio. For a wide range of pore sizes (e.g. 50 to thousands of Debye lengths) and a wide range of ion and fluid conditions, matched materials exhibit near-equal charge ratios. Certainly specific values would be determined for a particular combination of elements, fluid, fluid ionic content and load task. In many cases it is necessary to match a first larger-pored and high zeta potential material to a second finer-pored material. Generally matching requires a zeta potential of the second material that: 1) is the same sign as that of the first material, and 2) has a value that is about 1 to 2 times the ratio of the pore sizes (e.g. if the pore size of the second material is one-tenth that of the first material, then for a match the zeta potential of the second material will be in the range of about one-tenth to one-fifth that of the first material, the exact value depending of the zeta potential of the first material and other fluid and surface properties).

Suitable materials may be obtained through a combination of different solid materials and liquid compositions. For matched materials the sign of the zeta potentials must be the same. This follows from the rule that: for positive zeta potentials, $R < R_f$, whereas for negative zeta potentials, $R > R_f$.

Examples of suitable combinations of materials include, but are not limited to:

Under acidic conditions (i.e. pH values in the range of 3 to 5) silica displays a reduced negative zeta potential. Thus any of the well-known methods of making a porous silica element can be used to provide a low zeta potential material. High negative zeta potential in this pH range include: a material having sulfonic acid surface sites (negative potential).

At selected pH values ranging from nominally pH 3 to pH 9 alumino-silicates (e.g. an alumina-silica solgel or aerogel or zeolite) display reduced zeta potentials and these may be of either positive or negative sign depending on the composition. This may be used in combination with a variety of high zeta potential materials, including: silica having a high negative zeta potential at pH values greater than about 6; a material with sulfonic acid surface sites having a high negative zeta potential for pH values greater than about 2; a material having amine surface sites having a high positive zeta potential for pH values less than about 9.5.

Zwitterionic materials (i.e. having both positive and negative surface sites) display a reduced zeta potential over a range of pH values due to the presence of both types of ionized surface sites (e.g. for Nylon this occurs between about pH 5 and pH 8). For such materials, the degree to which the zeta potential is suppressed and the sign of the resulting zeta potential can be altered according to how the material was synthesized or by chemical post treatment or by the fluid composition. This may be used in combination with a variety of high zeta potential materials (see list immediately above).

In electrophoresis it is sometimes preferable to operate under a condition of little or no electroosmotic flow. To achieve this condition various methods have been widely reported for in situ derivatization or coating of capillaries and microconduits. These same methods can be applied to alter or reduce the zeta potential of a wide variety of silica-like, glassy and polymeric materials. These may be used in combination with a variety of high zeta potential materials (see list above).

Many production polymers are weakly charged or modified with some surface charge to promote wetting, including: various types of nylon, polyvinyledene fluoride, polysufones, polyether sulfones, mixed cellulose esters. These materials provide a wide range of both low positive and low negative zeta potentials. Further many of these materials are readily further derivatized, using standard methods, to further alter the sign and magnitude of the zeta potential. These may be used in combination with a variety of high zeta potential materials.

Geometry

Once the material specification and the geometry factor for the element are determined, four considerations go towards designing actual element geometry:

1) Mechanical strength for cases where pressure is present.

2) The required geometry factor determined from the optimization procedure.

3) Differential solute flux at the interface between an element and any junction fluid at the terminal ends of the element.

At a junction between a junction fluid and a porous material a differential solute flux (as discussed above in the material supporting equation 18) will exist if the charge transfer through porous material is to some degree ion selective. That is, the R-value for the porous elements may be matched but there is still a mismatch between this R-value and that of the fluid in any empty conduits. From the examples above: At the junction between the second and the third elements, materials were selected to minimize $R_2-R_3$ so as to minimize evolution of the working fluid. But this selection means that there may be a differential flux at the junction between the third element and the reservoir fluid, since the prior minimization may imply a non-zero value of $R-R_f$. Because the fluid at the third element—reservoir junction is generally stagnant, ion transport to/from the element may become diffusion limited. To minimize this effect the area of the element in contact with the reservoir is preferably increased.

4) Additional voltage drops between the ends of elements in electrical series. In addition to the performance reduction due to voltage drops discussed before, one may need to reduce the voltage drop across certain elements so as to tie the voltage in the fluid effluent as close as possible to a known potential (e.g. system electrical ground).

These considerations are different for:

EOF element—terminal reservoir junctions. The fluid in the reservoir is essentially stagnant, thus differential ion flux between an element and the junction fluid in the reservoir is a diffusion limited process. The element area is preferably increased at the reservoir to reduce this effect and also to reduce the voltage drop incurred between the element and the electrode. The electrode is preferably located near but not in direct contact with the bridge. This minimizes voltage drops and allows normal equilibrium chemistry to proceed in the fluid. The area increase at the reservoir end of the element is preferably by a factor of two and more preferably by a factor of at least 10 times. FIGS. 3 and 4 show possible configurations.

EOF element junctions at a working fluid source/sink reservoir. In this case, the load factor is large thus the materials and geometry are selected accordingly. The EOF element contact is made using the working fluid reservoir as a junction. The whole cross sectional area of the element connecting to the electrode reservoir area is preferably increased to provide a large ratio of geometry factors, to minimize diffusion layer thickness and to minimize voltage drop. FIG. 3 shows a possible junction where the first element width and thickness have been increased (relative to that of the second element). This figure also shows a further preferable construction where the EOF elements protrude into the reservoirs.

FIG. 4 shows a different possible junction. In this case fluid is siphoned from or pressure-driven to the working fluid reservoir. It is also desirable to layout the ends of the EOF elements so as to assure that the whole junction, and in particular the faces of the elements are exposed to flowing fluid. The spacing between the element ends is preferably minimized, so as to not incur further voltage drop. The area of the conduit connecting the junction and the working fluid reservoir is preferably increased to minimize empty conduit pressure drop, to promote good communication between the reservoir fluid and the flow elements, and to promote initial wetting.

EOF element junction at pressure or generally serving microconduits. In this case the load factor may be near unity and the EOF element material and geometry factors are selected accordingly. Under certain conditions the elements will be subject to a mechanical pressure, thus: the elements materials must be selected for suitable compressive strength; the means of retaining the elements in the conduit must be selected for suitable shear strength, and; the substrate and cover thickness and bonding method or fitting must be designed for suitable clamping strength. FIG. 5 shows one possible layout where the third element has been tapered from an intermediate cross-section at the microconduit junction (done to minimize diffusion layer thickness), to a smaller cross section in the middle (done to provide mechanical strength and meet geometry factor requirements) to a large cross section at the bridge reservoir junction (done to minimize diffusion layer thickness). A further reason for varying the junction shape is found in expanding the relation for the respective geometry factors (i.e. expanding $g_2 = \epsilon g_3$).

$$\frac{L_3}{w_3} = \varepsilon \frac{L_2 h_2 F_2}{w_2 h_3 F_3} \quad (19)$$

For near-equal depths, h, and formation factors, and for $\epsilon$ selected to be 10% (say), this gives the required first element length to width ratio at less than one-tenth that of the second element. This condition may be difficult to satisfy given the mechanical strength requirements as well as the reservoir layout requirements. Thus it may be preferable to:

1. Increase the width of the third element with respect to that of the second element at the microconduit junction. However a detailed consideration of the electrical field at the junction suggests that little further advantage in voltage drop is gained by increasing the width by more than a factor of 2 to 3 times. Increasing the width by large amounts also has the problem of substantially increasing the pressure force acting to shear/compress the element and to separate or fracture the substrate/cover.

2. Increase the depth of the third element, preferably by a factor of 2 to 5 times. However, greatly increasing the depth increases pressure force acting to shear/compress the element.

3. Taper the first element to introduce a geometric contribution that serves to reduce the element formation factor by a factor of 3 to 5 times.

4. Select the first element media formation factor less than that of the second element material. Preferably select a second element media formation factor that is relatively large (i.e. $F_2$ of 4 to 5) and a first element media formation factor that is relatively low (i.e. $F_3$ of 2 to 3).

Used in combination these tactics can be applied to increase the overall length of the third element by a factor of ten times or more and thus alleviate the layout difficulty while still meeting the design optimization goals.

5. Exemplary Embodiments of EOF Systems, Elements, Bridges and Junctions

Therefore, as the foregoing shows, in a preferred embodiment the invention provides an electroosmotic flow system comprising a first electroosmotic flow (EOF) element containing a first liquid and a second EOF element containing a second liquid in fluidic and electrical communication with the first EOF element, wherein the absolute value of the difference between the flux ratios of the first and second EOF elements is less than or equal to a target value, which, for example, may be about zero. In one embodiment of the EOF system, the first liquid and the second liquid comprise the same chemical components. Preferably, the first EOF element contains a porous material that is selected so that the absolute value of the difference between the flux ratios of the first and second EOF elements is less than or equal to a target value. Additionally, the second EOF element may contain a porous material. The EOF system may also comprise a reservoir containing a third liquid, wherein the reservoir is in fluid communication with the first and second EOF elements. Alternatively, the EOF system may also comprise an electrode reservoir containing a reservoir liquid and wherein the first EOF element is a bridge element connecting the electrode reservoir to the second EOF element. In a preferred embodiment of the EOF system, the magnitude of the charge ratio (absolute value of the charge ratio) of at least one of the two EOF elements is greater than about 0.1.

Additionally, the invention provides an electroosmotic flow system comprising a plurality of EOF elements in fluidic and electrical communication with each other, wherein the absolute value of the difference between the flux ratios of any two EOF elements is less than or equal to a target value. Preferably, the magnitude of the charge ratio of at least one of said plurality of EOF elements is greater than about 0.1.

In another embodiment, the invention provides a bridge element for connecting an electroosmotic flow element carrying a working fluid to an electrode reservoir containing the working fluid, wherein the flux ratio of the bridge element is substantially equal to the flux ratio of the electroosmotic flow element. Preferably, the magnitude of the charge ratio of the EOF element is greater than about 0.1. In one embodiment, the flow rate of working fluid flowing through the bridge element is substantially equal to zero. In various embodiments, the flow rate of working fluid flowing through the bridge element due to electroosmotic forces, and/or due to a pressure difference across the bridge element may be substantially equal to zero. Alternatively, the flow rate of working fluid flowing through the bridge element is less than 0.01%, 1%, or 10% of the flow rate through the EOF element. In a preferred embodiment, the voltage drop across the bridge element is substantially less than the voltage drop across the electroosmotic flow element, for example, the voltage drop across the bridge element is less than 10% of the voltage drop across the electroosmotic flow element. In various non-limiting, exemplary embodiments, the bridge element comprises a conduit, or contains a porous material. In one embodiment, the conduit comprises a plurality of channels.

In yet another embodiment, the invention provides an electroosmotic flow system through which a working fluid flows comprising an electroosmotic flow element having a first terminal portion and a second terminal portion, a first bridge element having a first terminal portion and a second terminal portion, a first electrode and a second electrode electrically connected to a source of current, a first electrode reservoir containing the first electrode and the working fluid, wherein the first electrode is in contact with the working fluid and wherein the first terminal portion of the first bridge element is in contact with the working fluid in the electrode reservoir, a first junction containing a junction liquid wherein the second terminal portion of the first bridge element and the first terminal portion of the electroosmotic flow element are in contact with the junction liquid, and a connection for connecting the second electrode to the second terminal portion of the electroosmotic flow element, wherein the flux ratio of the first bridge element is substantially equal to the flux ratio of the electroosmotic flow element. Preferably, the magnitude of the charge ratio of the EOF element is greater than about 0.1. In one embodiment, the connection for connecting the second electrode to the second terminal portion of the electroosmotic flow element further comprises a second bridge element having a first terminal portion and a second terminal portion, a second electrode reservoir containing the second electrode and the working fluid, wherein the second electrode is in contact with the working fluid and wherein the second terminal portion of the second bridge element is in contact with the working fluid in the second electrode reservoir, and a second junction containing a second junction liquid, wherein the second terminal portion of the electroosmotic flow element and the first terminal portion of the second bridge element are in contact with the second junction liquid, wherein the flux ratio of the second bridge element is substantially equal to the flux ratio of the electroosmotic flow element. Preferably, the surface area of the second terminal portion of the first bridge element is substantially greater than the effective cross section area of the first bridge element, for example, the surface area of the second terminal portion of the first bridge element is at least 50% greater than the effective cross section area of the first bridge element, or the surface area of the second terminal portion of the first bridge element is at least 100% greater than the effective cross section area of the first bridge element, or the surface area of the second terminal portion of the first bridge element is at least 200% greater than the effective cross section area of the first bridge element, or the surface area of the second terminal portion of the first bridge element is five to ten times the effective cross section area of the first bridge element. Further, preferably, the surface area of the first terminal portion of the electroosmotic flow element is substantially greater than the effective cross section area of the electroosmotic flow element. In another embodiment, the surface area of the second terminal portion of the second bridge element is substantially greater than the effective cross section area of the first bridge element.

Additionally, the invention provides an electroosmotic flow system through which a working fluid flows comprising a junction containing a junction liquid and an electroosmotic flow element having a terminal portion in contact with the junction liquid in said junction, wherein the surface area of said terminal portion in contact with the junction liquid is substantially greater than the effective cross section area of the electroosmotic flow element. Preferably, the magnitude of the charge ratio of the EOF element is greater than about 0.1. In various embodiment, the surface area of the terminal portion in contact with the junction liquid is 50%, 100%, or 200% greater than the effective cross section area of the electroosmotic flow element, or five to ten times the effective cross section area of the electroosmotic flow element. The EOF system may further comprise one or more electroosmotic flow elements, each of said electroosmotic flow elements having a terminal portion in contact with the junction liquid in said junction, wherein the surface area of the terminal portion of at least one of said electroosmotic flow elements in contact with the junction liquid is substantially greater than the effective cross section area of said electroosmotic flow element. In one embodiment, the magnitude of the charge ratio of at least one of the EOF elements is greater than about 0.1.

Additionally, the invention provides an electroosmotic flow system through which a working fluid flows, the electroosmotic flow system comprising a junction containing a junction liquid, and a bridge element having a terminal portion in contact with the junction liquid, wherein the surface area of said terminal portion in contact with the junction liquid is substantially greater than the effective cross section area of the bridge element. In various embodiments, the surface area of said terminal portion in contact with the junction liquid is 50%, 100%, or 200% greater than the effective cross section area of the bridge element, or is five to ten times the effective cross section area of the bridge element. The one embodiment, the EOF system further comprises one or more electroosmotic flow elements, each of said electroosmotic flow elements having a terminal portion in contact with the junction liquid in said junction, wherein the surface area of the terminal portion of at least one of said electroosmotic flow elements is substantially greater than the effective cross section area of said electroosmotic flow element. Preferably, the magnitude of the charge ratio of at least one of the EOF elements is greater than about 0.1.

The invention further provides an electroosmotic flow system through which a working fluid flows, the electroosmotic flow system comprising a junction containing a junction liquid, and a first electroosmotic flow element having a second terminal portion in contact with the junction liquid in said junction, and a second electroosmotic flow element having a first terminal portion in contact with the junction liquid in said junction, wherein the distance between the first terminal portion and the second terminal portion is less than the largest dimension of the first terminal portion and is less than the largest dimension of the second terminal portion. In one embodiment, the magnitude of the charge ratio of at least one of the EOF elements is greater than about 0.1. Preferably, the mean flow streamline through the junction has a substantial component that is tangential to the first terminal portion of the second EOF element.

Additionally, the invention provides an electroosmotic flow system through which a working fluid flows, the electroosmotic flow system comprising a junction containing a junction liquid, and a first electroosmotic flow element having a second terminal portion in contact with the junction liquid in said junction, and a second electroosmotic flow element having a first terminal portion in contact with the junction liquid in said junction, wherein the mean flow streamline through the junction has a substantial component that is tangential to the first terminal portion of the second EOF element. Preferably, the magnitude of the charge ratio of at least one of the EOF elements is greater than about 0.1. In one embodiment, the distance between the first terminal portion and the second terminal portion is less than the largest dimension of the first terminal portion and is less than the largest dimension of the second terminal portion.

The invention further provides a method for connecting an electroosmotic flow element having a first terminal portion and a second terminal portion and carrying a working fluid to a first electrode and a second electrode wherein current flows through the electroosmotic flow element when the two electrodes are connected to a source of current, the method comprising placing the first electrode in a first electrode reservoir containing the working fluid, connecting a bridge element having a first terminal portion and a second terminal portion by placing the first terminal portion of the bridge element in the first electrode reservoir, connecting the second terminal portion of the bridge element to the first terminal portion of the electroosmotic flow element, and connecting the second terminal portion of the electroosmotic flow element to the second electrode, wherein the bridge element is selected so that the flux ratio of the bridge element is substantially equal to the flux ratio of the electroosmotic flow element. Preferably, the magnitude of the charge ratio of the EOF element is greater than about 0.1. In one embodiment of the method, the bridge element is selected to have a pore size whereby the flux ratio of the bridge element is substantially equal to the flux ratio of the electroosmotic flow element. Alternatively, the bridge element is selected to have a zeta potential whereby the flux ratio of the bridge element is substantially equal to the flux ratio of the electroosmotic flow element. Further, preferably, the bridge element with the smallest pore size is selected from a group of bridge elements having flux ratios substantially equal to the flux ratio of the electroosmotic flow element.

Additionally, the invention provides an electroosmotic flow system through which a working fluid flows comprising a junction containing a junction liquid, and an electroosmotic flow element having a terminal portion in contact with the junction liquid, wherein the surface of said terminal portion is serrated whereby the surface area of said surface is substantially greater than the effective cross section area of the electroosmotic flow element. Preferably, the magnitude of the charge ratio of the EOF element is greater than about 0.1. In various embodiments, the aspect ratio of the serrations is greater than about 0.25 or less than about 4.

In another embodiment, the invention provides an electroosmotic flow system through which a working fluid flows, the electroosmotic flow system comprising a junction containing a junction liquid, and an electroosmotic flow element having a terminal portion in contact with the junction liquid, wherein the electroosmotic flow element is comprised of two materials, a first material having a first charge ratio comprising said terminal portion of the electroosmotic flow element in contact with said junction liquid and a second material having a second charge ratio comprising the remainder of the electroosmotic flow element. Preferably, the magnitude of the charge ratio of at least one of the materials is greater than about 0.1. Additionally, the first material may be selected so that the first charge ratio is of the same sign as the second charge ratio. In one embodiment, the first material is selected so that the value of the first charge ratio is greater than about ¼ the value of the second charge ratio but less than about ¾ of the value of the second charge ratio. Alternatively, the first material is selected so that the value of the first charge ratio is about half the value of the second charge ratio. In another embodiment of the flow system, the electroosmotic flow element further comprises one or more materials other than the first and the second materials, wherein each of said one or more materials is characterized by a charge ratio for said material.

In another embodiment, the invention provides a system for determining the difference in flux ratios of a first electroosmotic flow element and a second electroosmotic flow element comprising a first electrode and a second electrode electrically connected to a source of current whereby a current flows between the two electrodes at a system current value, a first electrode reservoir containing the first electrode and an electrolytic solution having a first concentration of the electrolyte, wherein the first electrode is in contact with said electrolyte, the first electroosmotic flow element, wherein the first terminal portion of said first electroosmotic flow element is in contact with said electrolytic solution whereby the electrolytic solution flows through the first electroosmotic flow element at a first flow rate, a second electrode reservoir containing said electrolyte at said first concentration, a second electrode placed inside the second electrode reservoir, the second electroosmotic flow element, wherein the second terminal portion of said second electroosmotic flow element is in electrical contact with said second electrode whereby the electrolytic solution flows through the second electroosmotic flow element at a second flow rate that is substantially less than the first flow rate, and a junction having a first inlet and a first outlet and a second outlet, wherein the second terminal portion of said first electroosmotic flow element is connected to said inlet, the first terminal portion of said second electroosmotic flow element is connected to said second outlet and wherein the electrolytic solution flows out of the first outlet at an outlet flow rate and a second concentration of the electrolyte. In one embodiment of the system, the magnitude of the charge ratio of at least one of the EOF elements is greater than about 0.1.

Additionally, the invention provides a method for determining the difference in flux ratios of a first electroosmotic flow element and a second electroosmotic flow element using the above-described system, the method comprising subtracting the first concentration from the second concentration to generate a concentration differential, multiplying the concentration differential by the outlet flowrate and the value of the electron charge to generate a product, and dividing the product by the system current value to generate the difference in flux ratios of the first electroosmotic flow element and the second electroosmotic flow element.

All of the publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. An electroosmotic flow (EOF) system comprising
  (A) a first electroosmotic flow (EOF) element which
   (a) contains a first liquid throughout its length,
   (b) has a first terminal portion A1 and a second terminal portion A2, and
   (c) has a first flux ratio $R_1$;
  (B) a second EOF element which
   (a) contains a second liquid throughout its length,
   (b) has a first terminal portion B1 and a second terminal portion B2, and
   (c) has a second flux ratio $R_2$ which is from about $0.95R_1$ to about $1.05R_1$; and (C) a junction
  (a) at which the terminal portions A2 and B1 terminate, and
  (b) which contains a junction liquid in liquid and electrical communication with the first and second liquids;
the first and second EOF elements having different charge ratios, and at least one of the first and second EOF elements having a charge ratio whose magnitude is greater than about 0.1.

2. An EOF system according to claim 1 wherein the difference between $R_1$ and $R_2$ is about zero.

3. An EOF system according to claim 1 wherein the first liquid and the second liquid comprise the same chemical components.

4. An electroosmotic flow (EOF) system according to claim 1 further comprising
(D) an electrode reservoir
  (a) which contains a reservoir liquid and an electrode in contact with the reservoir liquid, and
  (b) at which the terminal portion A1 terminates;
whereby the first EOF element is a bridge element connecting the electrode reservoir to the junction.

5. An EOF system according to claim 4 which is in operation and wherein the first liquid has a flow rate through the bridge element which is substantially equal to zero.

6. An EOF system according to claim 4 which is in operation and wherein the first liquid has a flow rate through the bridge element which is less than 1% of the flow rate through the second EOF element.

7. An EOF system according to claim 4 which is in operation and wherein there is a voltage drop across the bridge element which is less than 10% of the voltage drop across the second EOF element.

8. An EOF system according to claim 1 wherein the terminal portion A2 comprises an empty conduit, and, when the system is in operation, current passes into or out of the conduit over an area which is at least 50% greater than the effective cross-section area of the first EOF element.

9. An EOF system according to claim 1 wherein the terminal portion A2 comprises a flow-impermeable boundary and a porous material, and the porous material has a face which is exposed to the junction liquid and which has a surface area at least 100% greater than the effective cross-section of the first EOF element, any microscopic irregularities of the face having a length scale less than about 100 Debye lengths being treated as smooth in determining the surface area of the face.

10. An EOF system according to claim 9 wherein the surface area of the face of porous material in the terminal portion A2 is at least 200% greater than the effective cross-section area of the first EOF element.

11. An EOF system according to claim 9 wherein the surface area of the face of the porous material in the terminal portion A2 is 5 to 10 times the effective cross-section area of the first EOF element.

12. An EOF system according to claim 1 wherein the terminal portion B1 comprises a flow-impermeable boundary and a porous material, and the porous material in the terminal portion B1 has a face which is exposed to the junction liquid and which has a surface area at least 100% greater than the effective cross-section of the second EOF element, any microscopic irregularities of the face having a length scale less than about 100 Debye lengths being treated as smooth in determining the surface area of the face.

13. An EOF system according to claim 12 wherein the surface area of the face of porous material in the terminal portion B1 is at least 200% greater than the effective cross-section area of the second EOF element element.

14. An EOF system according to claim 12 wherein the surface area of the face of the porous material in the terminal portion B1 is 5 to 10 times the effective cross-section area of the second EOF element.

15. An EOF system according to claim 1 wherein the distance between the terminal portions A2 and B1 is less than the largest dimension of the terminal portion B1 and less than the largest dimension of the terminal portion A2.

16. An EOF system according to claim 1 which is in operation and wherein the junction liquid has a mean flow streamline through the junction which has a substantial component tangential to the first terminal portion B1 of the second EOF element.

17. An EOF system according to claim 1 wherein at least one of the terminal portions A2 and B1 comprises a porous material having a serrated surface in contact with junction liquid.

18. An EOF system according to claim 17 wherein the aspect ratio of the serrations is greater than about 0.25.

19. An EOF system according to claim 17 wherein the aspect ratio of the serrations is less than about 4.

20. An EOF system according to claim 1 wherein at least one the first and second EOF elements comprises (i) a terminal portion which is composed of the first porous material, whereby the terminal portion has a first charge ratio, and (ii) a second portion which is composed of the second porous material, whereby the second portion has a second charge ratio which is different from the first charge ratio.

21. An EOF system according to claim 20 wherein the first charge ratio has the same sign as the second charge ratio, and the value of the first charge ratio is greater than about ¼ the value of the second charge ratio and less than about ¾ the value of the second charge ratio.

22. An EOF system according to claim 1 wherein one of the first and second EOF elements contains a porous material and the other of the first and second EOF elements is empty.

23. An EOF system according to claim 1 wherein the first EOF element contains a first porous material and the second EOF element contains a second porous material which is different from the first porous material.

24. An EOF system according to claim 1 wherein at least one of the EOF elements comprises a flow-impermeable boundary, and the cross-sectional area enclosed by the boundary at one or both of the terminal portions of that EOF element is greater than the limiting cross-section of that EOF element.

25. An EOF system according to claim 1 which is in operation and wherein
  (i) the first and second EOF elements are connected in electrical series and carry the same current,
  (ii) any liquid flow between the first EOF element and the junction is into the junction, and
  (iii) liquid flows out of the junction into the second EOF element.

26. An EOF system according to claim 1 wherein the junction has a negligible charge ratio.

27. An EOF system according to claim 1 wherein the first EOF element contains a first porous material having a first pore size $P_1$ and a first zeta potential $Z_1$, and the second EOF element contains a second porous material having a second pore size $P_2$ and a second zeta potential $Z_2$ which has the same sign as $Z_1$ and is from $Z_1.P_2/P_1$ to 2. $Z_1.P_2/P_1$.

28. An EOF system according to claim 1 which comprises a reservoir of working liquid in liquid communication with the junction.

29. An EOF system according to claim 28 which is in operation and wherein working liquid is supplied from the reservoir to the junction.

30. An electroosmotic flow (EOF) system comprising:
(A) a first electroosmotic flow (EOF) element which
  (a) contains a first liquid throughout its length,
  (b) has a first terminal portion A1 and a second terminal portion A2, and
  (c) has a first flux ratio $R_1$;
(B) a second EOF element which
  (a) contains a second liquid throughout its length,
  (b) has a first terminal portion B1 and a second terminal portion B2, and
  (c) has a second flux ratio $R_1$ which is from about $0.95R_1$ to about $1.05R_1$;
(C) a junction
  (a) at which the terminal portions A2 and B1 terminate, and
  (b) which contains a junction liquid in liquid and electrical communication with the first and second liquids;
(D) an electrode reservoir
  (a) which contains a reservoir liquid and a first electrode in contact with the reservoir liquid, and
  (b) at which the terminal portion A1 terminates;
(E) a second electrode which is electrically connected to the terminal portion B2; and
(F) a source of current connected to the first and second electrodes;
whereby the first EOF element is a bridge element connecting the electrode reservoir to the junction, and, if the first and second electrodes are connected to a source of electrical power, the first and second EOF elements are connected in electrical series and carry the same current;
the first and second EOF elements having different charge ratios, and at least one of the first and second EOF elements having a charge ratio whose magnitude is greater than about 0.1.

31. An EOF system according to claim 30 which further comprises
(G) a third EOF element which
  (a) contains a third liquid throughout its length, and
  (b) has a first terminal portion C1 and a second terminal portion C2;
(H) a second junction
  (a) at which the terminal portions B2 and C1 terminate, and
  (b) which contains a second junction liquid in liquid and electrical communication with the second and third liquids; and
(I) a second electrode reservoir
  (a) which contains a second reservoir liquid and the second electrode in contact with the second reservoir liquid, and
  (b) at which the terminal portion C2 terminates;
whereby
(a) the third EOF element is a second bridge element connecting the second electrode reservoir to the second junction, and
(b) if the first and second electrodes are connected to a source of electrical power,
  (i) the first, second and third EOF elements are connected in electrical series and carry the same current,
  (ii) any liquid flow between the first EOF element and the junction is into the junction, and
  (iii) liquid flows out of the junction into the second EOF element.

32. An EOF system according to claim 31 wherein each of the first and second junctions has a negligible charge ratio.

33. An EOF system according to claim 31 which comprises a reservoir of working fluid in liquid communication with the first junction.

34. An EOF system according to claim 33 which is in operation and wherein working fluid is supplied from the reservoir to the first junction.

35. An EOF system according to claim 30 wherein the second terminal portion A2 of the bridge element comprises an empty conduit, and, when the system is in operation, current passes into or out of the conduit over an area which is at least 50% greater than the effective cross-section area of the bridge element.

36. An EOF system according to claim 30 wherein the second terminal portion A2 of the bridge element comprises a flow-impermeable boundary and a porous material, and the porous material has a face which is exposed to the junction liquid and which has a surface area is at least 100% greater than the effective cross-section area of the bridge element, any microscopic irregularities of the face having a length scale less than about 100 Debye lengths being treated as smooth in determining the surface area of the face.

37. An EOF system according to claim 36 wherein the surface area of the face of the porous material 200% greater than the effective cross-section area of the bridge element.

38. An EOF system according to claim 36 wherein the surface area of the face of the porous material is five to ten times the effective cross-section area of the bridge element.

39. An EOF system according to claim 36 wherein the first terminal portion B1 of the second EOF element comprises a flow-impermeable boundary and a porous material, and the porous material of the terminal portion B1 has a face which is exposed to the junction liquid and which has a surface area at least 50% greater than the effective cross-section area of the second EOF element, any microscopic irregularities having a length scale less than about 100 Debye lengths being treated as smooth in determining the surface area of the face.

40. An EOF system according to claim 39 wherein
(1) the second terminal portion B2 of the second EOF element comprises a flow-impermeable boundary and a porous material, and the face of the porous material of the terminal portion B2 exposed to the second junction liquid has a surface area which is at least 50% greater than the effective cross-section area of the second EOF element, any microscopic irregularities of the face having a length scale less than about 100 Debye lengths being treated as smooth in determining the surface area of the face, and
(2) the first terminal portion C1 of the third EOF element comprises a flow-impermeable boundary and a porous material, and the the porous material of the terminal portion C1 having a face which is exposed to the second junction liquid and which has a surface area is substantially greater than the effective cross-section area of the third EOF element, any microscopic irregularities of the face having a length scale less than about 100 Debye lengths being treated as smooth in determining the surface area of the face.

41. An electroosmotic flow (EOF) system comprising
(A) an electroosmotic flow (EOF) element which
(a) contains a first liquid,
(b) has a charge ratio whose magnitude is greater than about 0.1, and
(c) has a terminal portion, and
(B) a junction
(a) at which the terminal portion terminates, and
(b) which contains a junction liquid in liquid and electrical communication with the first liquid;
the terminal portion comprising a flow-impermeable boundary and a porous material, the porous material having a face which is in contact with the junction liquid and which has a surface area substantially greater than the effective cross-section area of the EOF element, any microscopic irregularities having a length scale less than about 100 Debye lengths being treated as smooth in determining the geometric surface area of the face.

42. An EOF system according to claim 41 wherein the surface area of the face in contact with the junction liquid is at least 50% greater than the effective cross-section area of the EOF element.

43. An EOF system according to claim 41 wherein the surface area of the face in contact with the junction liquid is at least 100% greater than the effective cross-section area of the EOF element.

44. An EOF system according to claim 41 wherein the surface area of the face in contact with the junction liquid is at least 200% greater than the effective cross-section area of the EOF element.

45. An EOF system according to claim 41 wherein the surface area of the face in contact with the junction liquid is five to ten times the effective cross-section area of the EOF element.

46. An EOF system according to claim 41 which further comprises:
one or more additional EOF elements at least one of which has a terminal portion which
(a) terminates at the junction,
(b) comprises a flow-impermeable boundary and a porous material, the porous material having a face which is exposed to the junction liquid and which has a surface area substantially greater than the effective cross-section area of said additional EOF element, any microscopic irregularities having a length scale less than about 100 Debye lengths being treated as smooth in determining the surface area of the face.

47. An EOF system according to claim 41 wherein the EOF element is a bridge element.

48. An electroosmotic flow (EOF) system comprising
(A) a first electroosmotic flow (EOF) element which
(a) contains a first liquid throughout its length, and
(b) has a first terminal portion A1 and a second terminal portion A2; and
(B) a second EOF element which
(a) contains a second liquid throughout its length, and
(b) has a first terminal portion B1 and a second terminal portion B2; and
(C) a junction
(a) at which the terminal portions A2 and B1 terminate, and
(b) which contains a junction liquid which contacts the terminal portions A2 and B1 and is in liquid and electrical communication with the first and second liquids;
the first and second EOF elements having different charge ratios, and at least one of the first and second EOF elements having a charge ratio whose magnitude is greater than about 0.1; and
the distance between the terminal portions A2 and B1 being (i) less than the largest dimension of the first terminal portion B1 and (ii) less than the largest dimension of the second terminal portion A2.

49. An EOF system according to claim 48 which is in operation and wherein the junction liquid has a mean flow streamline through the junction which has a substantial component that is tangential to the first terminal portion B1 of the second EOF element.

50. An electroosmotic flow (EOF) system which is in operation and which comprises
(A) a first electroosmotic flow (EOF) element which
(a) contains a first liquid throughout its length, and
(b) has a first terminal portion A1 and a second terminal portion A2; and
(B) a second EOF element which
(a) contains a second liquid throughout its length, and
(b) has a first terminal portion B1 and a second terminal portion B2; and
(C) a junction
(a) at which the terminal portions A2 and B1 terminate, and
(b) which contains a junction liquid which contacts the terminal portions A2 and B1 and is in liquid and electrical communication with the first and second liquids;
the first and second EOF filaments having different charge ratios and at least one of the first and second EOF elements having a charge ratio whose magnitude is greater than about 0.1; and
the junction liquid having a mean flow streamline through the junction which has a substantial component that is tangential to the first terminal portion B1 of the second EOF element.

51. An electroosmotic flow system through which a working fluid flows, the electroosmotic flow system comprising:
a junction containing a junction liquid; and
an electroosmotic flow element having a terminal portion in contact with
junction liquid,
wherein the surface of said terminal portion is serrated whereby the surface area of said surface is substantially greater than the effective cross-section area of the electroosmotic flow element.

52. The electroosmotic flow system of claim 51, wherein the magnitude of the charge ratio of the EOF element is greater than about 0.1.

53. The electroosmotic flow system of claim 51, wherein the aspect ratio of the serrations is greater than about 0.25.

54. The electroosmotic flow system of claim 53, wherein the aspect ratio of the serrations is less than about 4.

55. An electroosmotic flow (EOF) system comprising:
(A) an electroosmotic flow (EOF) element which
(a) contains a first liquid throughout its length, and
(b) comprises (i) a terminal portion which is composed of a first porous material, whereby the terminal portion has a first charge ratio, and (ii) a second portion which is composed of a second porous material, whereby the second portion has a second charge ratio which is different from the first charge ratio, and (B) a junction
  (a) at which the terminal portion terminates, and
  (b) which contains a junction liquid which contacts the terminal portion.

56. An EOF system according to claim 55 wherein the magnitude of at least one of the first charge ratio and second charge ratio is greater than about 0.1.

57. An EOF system according to claim 55 wherein the the first charge ratio is of the same sign as the second charge ratio.

58. An EOF system according to claim 55 wherein the value of the first charge ratio is greater than about ¼ the value of the second charge ratio and less than about ¾ of the value of the second charge ratio.

59. An EOF system according to claim 55 wherein the value of the first charge ratio is about half the value of the second charge ratio.

60. An EOF system according to claim 55 wherein the EOF element further comprises one or more materials other than the first and the second materials.

61. A method for determining the difference between the flux ratio of a first electroosmotic flow element and the flux ratio of a second electroosmotic flow element, the method comprising
  (A) providing a system comprising
    a first electrode and a second electrode electrically connected to a source of current whereby a current flows between the two electrodes at a system current value;
    a first electrode reservoir containing the first electrode and an electrolytic solution having a first concentration of the electrolyte, wherein the first electrode is in contact with said electrolyte;
    the first electroosmotic flow element, wherein the first terminal portion of said first electroosmotic flow element is in contact with said electrolytic solution whereby the electrolytic solution flows through the first electroosmotic flow element at a first flow rate;
    a second electrode reservoir containing the second electrode and said electrolyte solution at said first concentration;
    the second electroosmotic flow element, wherein the second terminal portion of said second electroosmotic flow element is in electrical contact with said second electrode;
    whereby the electrolytic solution flows through the second electroosmotic flow element at a second flow rate that is substantially less than the first flow rate; and
    a junction having a first inlet and a first outlet and a second outlet, wherein the second terminal portion of said first electroosmotic flow element is connected to said inlet, the first terminal portion of said second electroosmotic flow element is connected to said second outlet and wherein the electrolytic solution flows out of the first outlet at an outlet flow rate and a second concentration of the electrolyte;
  (B) determining the difference between the first concentration and the second concentration, thus generating to a concentration differential;
  (C) determining the outlet flow rate;
  (D) multiplying the concentration differential by the outlet flow rate and the value of the electron charge to generate a product;
  (E) determining the system current value; and
  (F) dividing the product generated in step (D) by the system current value to generate the difference between the flux ratio of the first electroosmotic flow element and the flux ratio of the second electroosmotic flow element.

62. An electroosmotic flow (EOF) system which comprises
  (A) an EOF element having a terminal portion, and
  (B) a junction
    (a) at which the terminal portion terminates, and
    (b) which can be filled with a junction liquid;
  the terminal portion comprising a porous material having a face which
    (i) is in contact with the junction liquid when the junction is filled with the junction liquid, and
    (ii) comprises serrations.

63. An EOF system according to claim 62 wherein the face of the porous material comprises serrations having an aspect ratio greater than about 0.25 and less than about 4.

64. An electroosmotic flow (EOF) system which comprises
  (A) an electroosmotic flow (EOF) element comprising a terminal portion; and
  (B) a junction
    (a) at which the terminal portion terminates, and
    (b) which can be filled with a junction liquid;
  the EOF element comprising
    (a) a conduit having a flow-impermeable boundary, and
    (b) a porous material within the boundary, the porous material extending beyond an end of the boundary at the terminal portion and having a face which is in contact with the junction liquid when the junction is filled with junction liquid.

65. An electroosmotic flow (EOF) system which comprises
  (A) an electroosmotic flow (EOF) element comprising
    (a) a terminal portion having a first cross-section and
    (b) a second portion having a second cross-section which is substantially smaller than the first cross-section; and
  (B) a junction
    (a) at which the terminal portion terminates, and
    (b) which can be filled with a junction liquid;
  the terminal portion comprising
    (a) a conduit having a flow-impermeable boundary, and
    (b) a porous material within the boundary,
  the porous material extending at least to an end of the boundary and providing a face which is in contact with the junction liquid when the junction is filled with junction liquid.

66. An EOF system according to claim 65 wherein the porous material extends beyond the end of the boundary and into the junction.

67. An EOF system according to claim 65 wherein the terminal portion contains a first porous material and a second portion of the EOF element contains a second porous material.

68. An electroosmotic flow (EOF) system comprising
  (A) a first electroosmotic flow (EOF) element which
    (a) contains a first liquid throughout its length,
    (b) has a first terminal portion A1 and a second terminal portion A2, and
    (c) has a first flux ratio $R_1$;
  (B) a second EOF element which
    (a) contains a second liquid throughout its length,
    (b) has a first terminal portion B1 and a second terminal portion B2, and
    (c) has a second flux ratio $R_2$ which is from about $0.95R_1$ to about $1.05R_1$;

(C) a third EOF element which
  (a) contains a third liquid throughout its length, and
  (b) has a first terminal portion C1 and a second terminal portion C2;
(D) a first junction
  (a) at which the terminal portions A2 and B1 terminate, and
  (b) which contains a first junction liquid in liquid and electrical communication with the first and second liquids;
(E) a second junction
  (a) at which the terminal portions B2 and C1 terminate, and
  (b) which contains a second junction liquid in liquid and electrical communication with the second and third liquids;
(F) a first electrode reservoir which
  (a) contains a reservoir liquid and a first electrode in contact with the reservoir liquid, and
  (b) at which the terminal portion A1 terminates;
(G) a second electrode reservoir which
  (a) contains a second reservoir liquid and a second electrode in contact with the second reservoir liquid, and
  (b) at which the terminal portion C2 terminates;
(H) a supply reservoir which
  (a) contains a working liquid, and
  (b) is in liquid communication with the first junction; and
(I) an outlet from the second junction;
whereby, if the first and second electrodes are connected to a source of electrical power,
  (i) the first and second EOF elements are connected in electrical series and carry the same current,
  (ii) any liquid flow between the first EOF element and the first junction is into the first junction, and
  (iii) liquid flows out of the first junction into the second EOF element;
the first and second EOF elements having different charge ratios, and at least one of the first and second EOF elements having a charge ratio whose magnitude is greater than about 0.1.

69. An EOF system according to claim 68 which is in operation and wherein working liquid is supplied from the supply reservoir to the first junction, and liquid is removed from the second junction through the outlet.

70. An EOF system according to claim 68 wherein
(a) the first EOF element comprises
  (i) a first conduit having a flow-impermeable boundary, and
  (ii) a first porous material within the boundary, the first porous material extending beyond the boundary at the terminal portion A2 and having a face which is in contact with the first junction liquid; and
(b) the second EOF element comprises
  (i) a second conduit having a flow-impermeable boundary, and
  (ii) a second porous material within the boundary, the second porous material extending beyond an end of the boundary at the terminal portion 81 and having a face which is in contact with the first junction liquid.

71. An EOF system according to claim 70 wherein
(a) the face of the porous material extending beyond the boundary at the terminal portion A2 has a surface area at least 100% greater than the effective cross-section of the first EOF element, any microscopic irregularities of the face having a length scale less than about 100 Debye lengths being treated as smooth in determining the surface area of the face; and
(b) the face of the porous material extending beyond the boundary at the terminal portion B1 has a surface area at least 100% greater than the effective cross-section of the second EOF element, any microscopic irregularities of the face having a length scale less than about 100 Debye lengths being treated as smooth in determining the surface area of the face.

72. An EOF system according to claim 70 wherein the first porous material has a first pore size $P_1$ and a first zeta potential $Z_1$, and the second porous material has a second pore size $P_2$ and a second zeta potential $Z_2$ which has the same sign as $Z_1$ and is from $Z_1.P_2/P_1$ to $2.Z_1.P_2/P_1$.

73. An EOF system according to claim 68 wherein the first junction has a negligible charge ratio.

74. An EOF system according to claim 68 which is in operation and wherein the first liquid has a flow rate through the first EOF element which is less than 1% of the flow rate through the second EOF element.

75. An EOF system according to claim 68 which is in operation and wherein there is a voltage drop across the first EOF element which is less than 10% of the voltage drop across the second EOF element.

* * * * *